United States Patent
Dubey et al.

(10) Patent No.: US 11,545,245 B1
(45) Date of Patent: Jan. 3, 2023

(54) PRESCRIPTION DRUG FULFILLMENT SYSTEM AND METHOD

(71) Applicant: AbbVie Inc., North Chicago, IL (US)

(72) Inventors: Pankaj Dubey, Lake Villa, IL (US); Vaibhav Jindal, Waukegan, IL (US)

(73) Assignee: ABBVIE INC., North Chicago, IL (US)

( * ) Notice: Subject to any disclaimer, the term of this patent is extended or adjusted under 35 U.S.C. 154(b) by 234 days.

(21) Appl. No.: 16/842,406

(22) Filed: Apr. 7, 2020

Related U.S. Application Data

(60) Provisional application No. 62/830,905, filed on Apr. 8, 2019.

(51) Int. Cl.
| | |
|---|---|
| *G16H 20/10* | (2018.01) |
| *G16H 10/60* | (2018.01) |
| *G06Q 40/08* | (2012.01) |
| *G06Q 30/02* | (2012.01) |
| *G06Q 20/40* | (2012.01) |
| *G06Q 10/10* | (2012.01) |
| *G06F 8/60* | (2018.01) |

(52) U.S. Cl.
CPC .............. *G16H 20/10* (2018.01); *G06Q 10/10* (2013.01); *G06Q 20/40* (2013.01); *G06Q 30/0283* (2013.01); *G06Q 40/08* (2013.01); *G16H 10/60* (2018.01); *G06F 8/60* (2013.01)

(58) Field of Classification Search
CPC .......... G16H 20/10; G16H 10/60; G06F 8/60; G06Q 10/10; G06Q 20/40; G06Q 30/0283; G06Q 40/08
USPC ........................................................ 705/2–4
See application file for complete search history.

(56) References Cited

U.S. PATENT DOCUMENTS

| | | |
|---|---|---|
| 5,597,995 A | 1/1997 | Williams et al. |
| 7,111,780 B2 | 9/2006 | Broussard et al. |
| 7,426,474 B2 | 9/2008 | Schoenbaum et al. |
| 10,438,693 B1 * | 10/2019 | Vandervoort .......... G16H 10/60 |
| 10,475,140 B2 | 11/2019 | Patel et al. |
| 2004/0225527 A1 | 11/2004 | Holz |
| 2011/0257989 A1 * | 10/2011 | Kumar .................... G16H 20/10 705/2 |
| 2013/0217982 A1 * | 8/2013 | Behzadi ................. G16H 20/10 600/302 |
| 2013/0317835 A1 * | 11/2013 | Mathew .................. G16H 20/10 705/2 |
| 2014/0039911 A1 | 2/2014 | Iyer |
| 2014/0358578 A1 | 12/2014 | Ptachcinski |
| 2016/0378931 A1 * | 12/2016 | Vaamonde ............. G16H 70/20 705/2 |
| 2019/0304597 A1 * | 10/2019 | Grossman .......... G06Q 30/0283 |

* cited by examiner

*Primary Examiner* — Mark Holcomb
(74) *Attorney, Agent, or Firm* — Armstrong Teasdale LLP

(57) ABSTRACT

A system for fulfilling a prescription is provided. The system may include at least one processor programmed to (i) receive a prescription request including patient data relating to a patient, (ii) determine an insurance provider of the patient based on the received patient data, (iii) determine an insured cost for a prescription for the patient, (iv) determine a non-insured cost for the prescription for the patient, (v) compare the insured cost to the non-insured cost to determine which cost is lower, (vi) depending on which cost is lower, i) send a message to the patient with a corresponding recommendation, and ii) process an insurance claim and/or a payment transaction upon authorization from the patient, and (vii) transmit the prescription to a pharmacy for further processing.

20 Claims, 22 Drawing Sheets

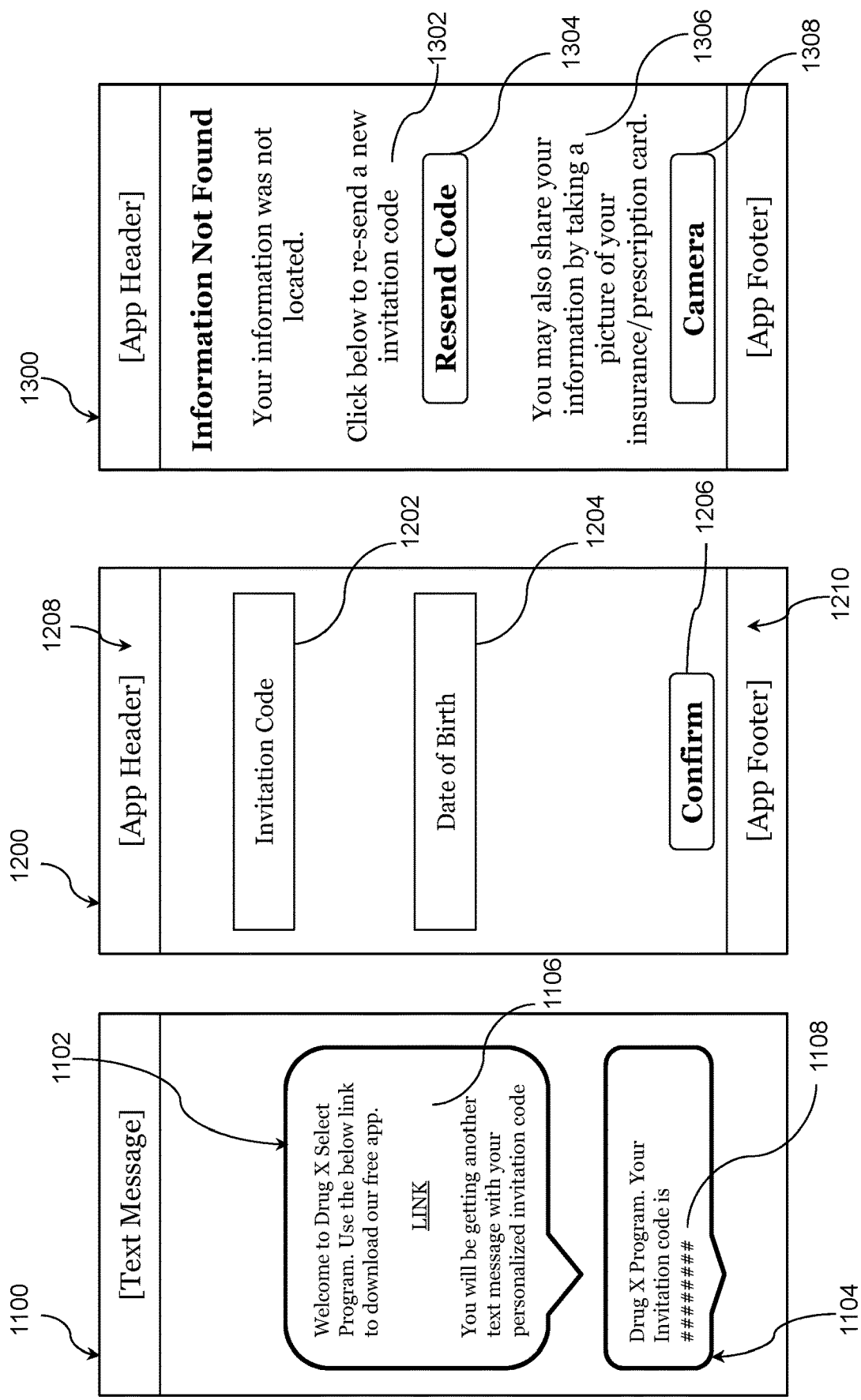

[App Header]

Edit and Confirm Details — 1402

- Thomas — 1404
- Anderson — 1406
- 01/01/1981 — 1408
- ABC Street — 1410
- Address Line 2 — 1412
- 60089 — 1414
- AA — 1416

[Confirm] — 1418

[App Footer]

[App Header]

Edit and Confirm Details

Your Insurance Company
Subscriber Name
Thomas Anderson
ID #: XXXXXX
Group #: XXXXXX — 1502

[Confirm] — 1504

[App Footer]

[App Header] — 1602

Terms of Use

These Online Terms of Use govern your access to Drug X Select Program, managed by Company X — 1604

:

[Accept] — 1606

[App Footer]

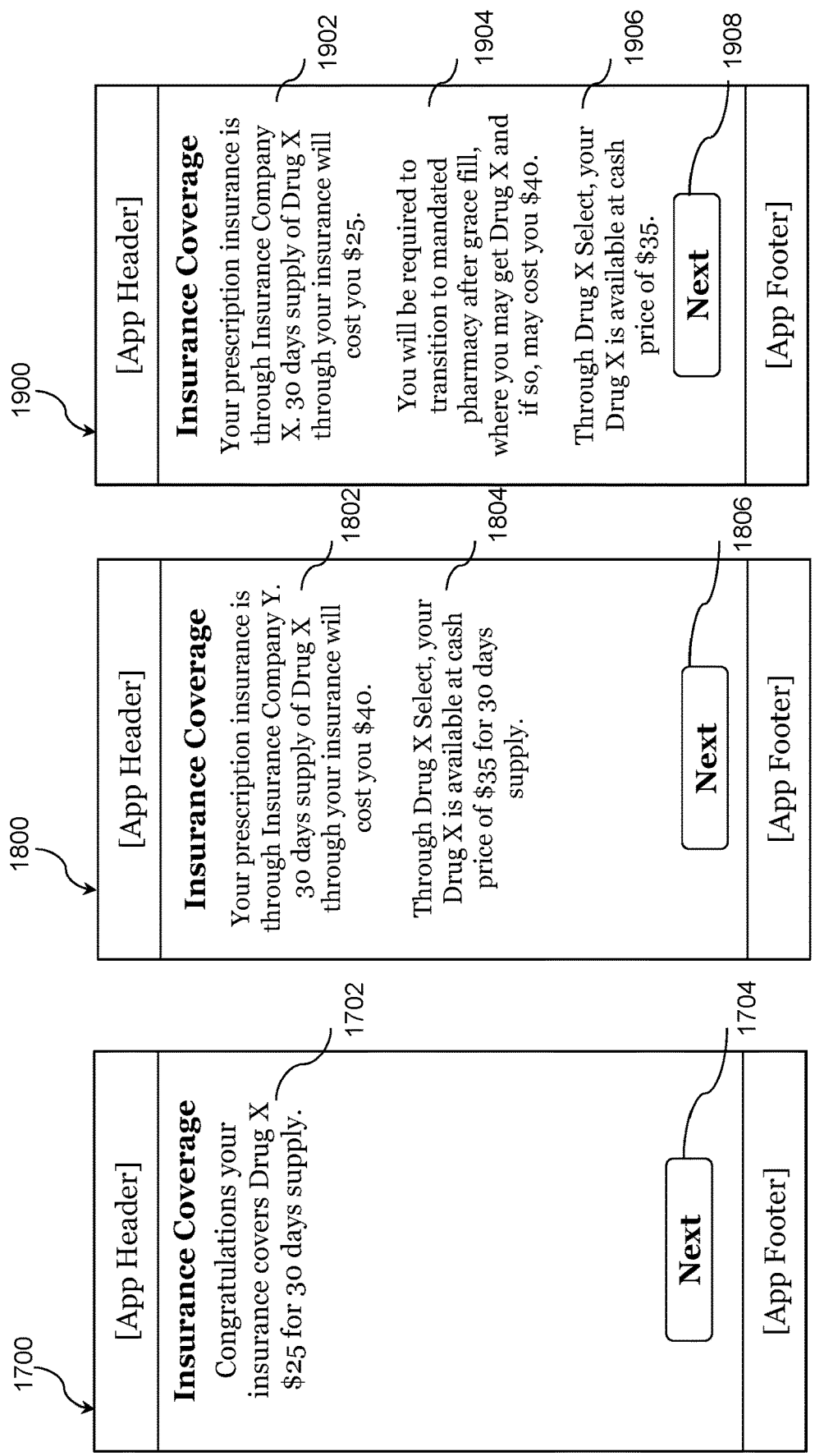

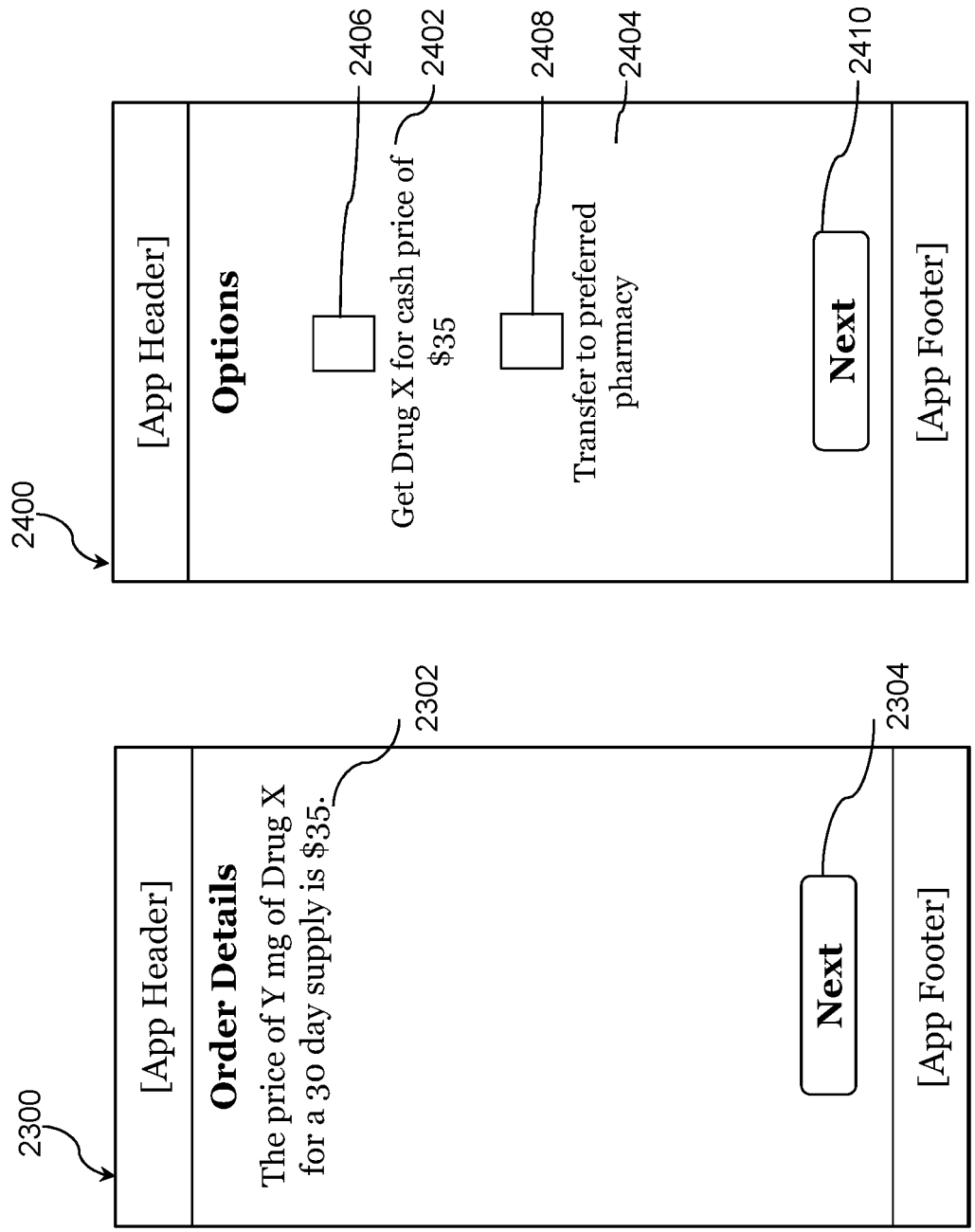

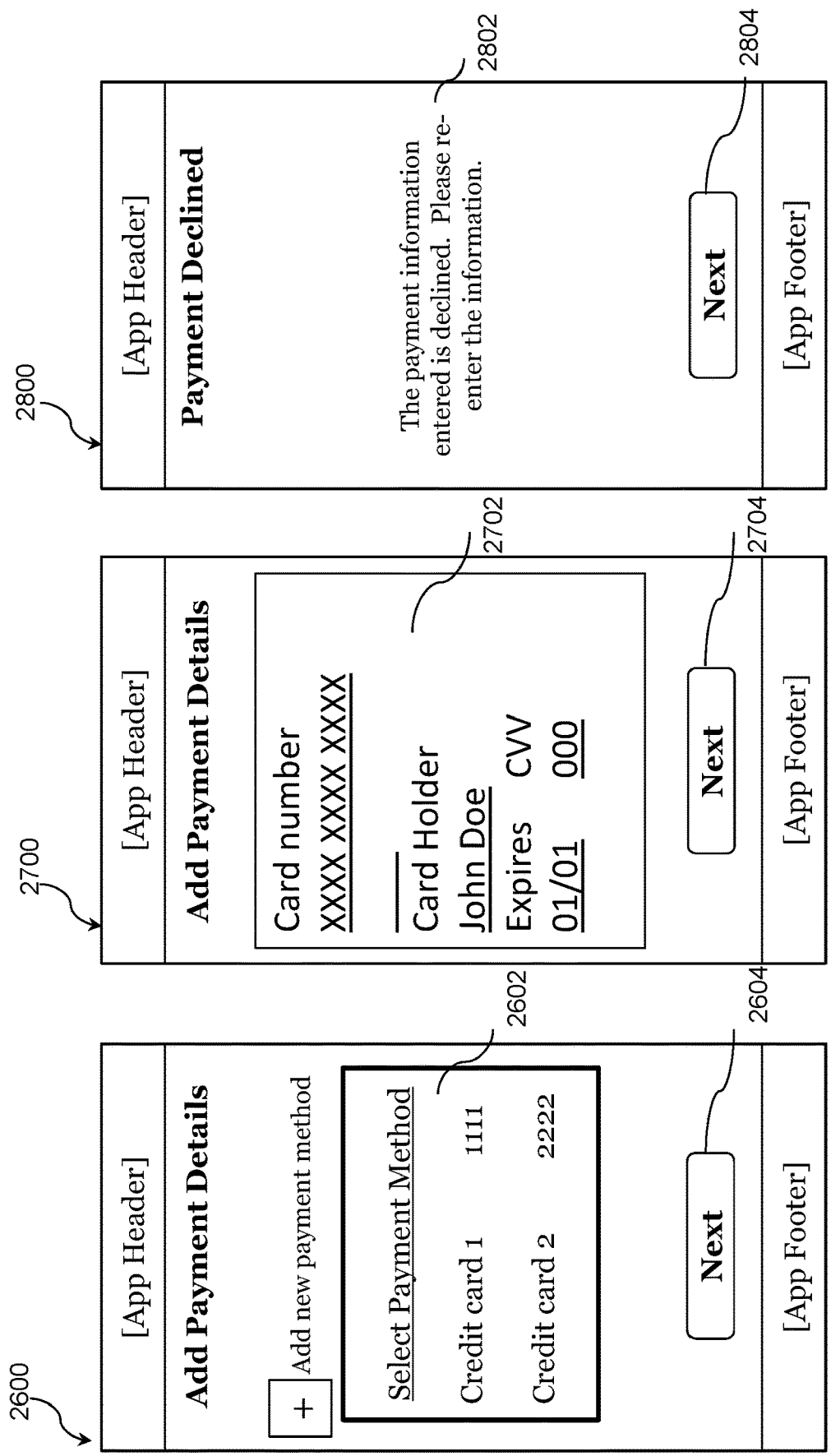

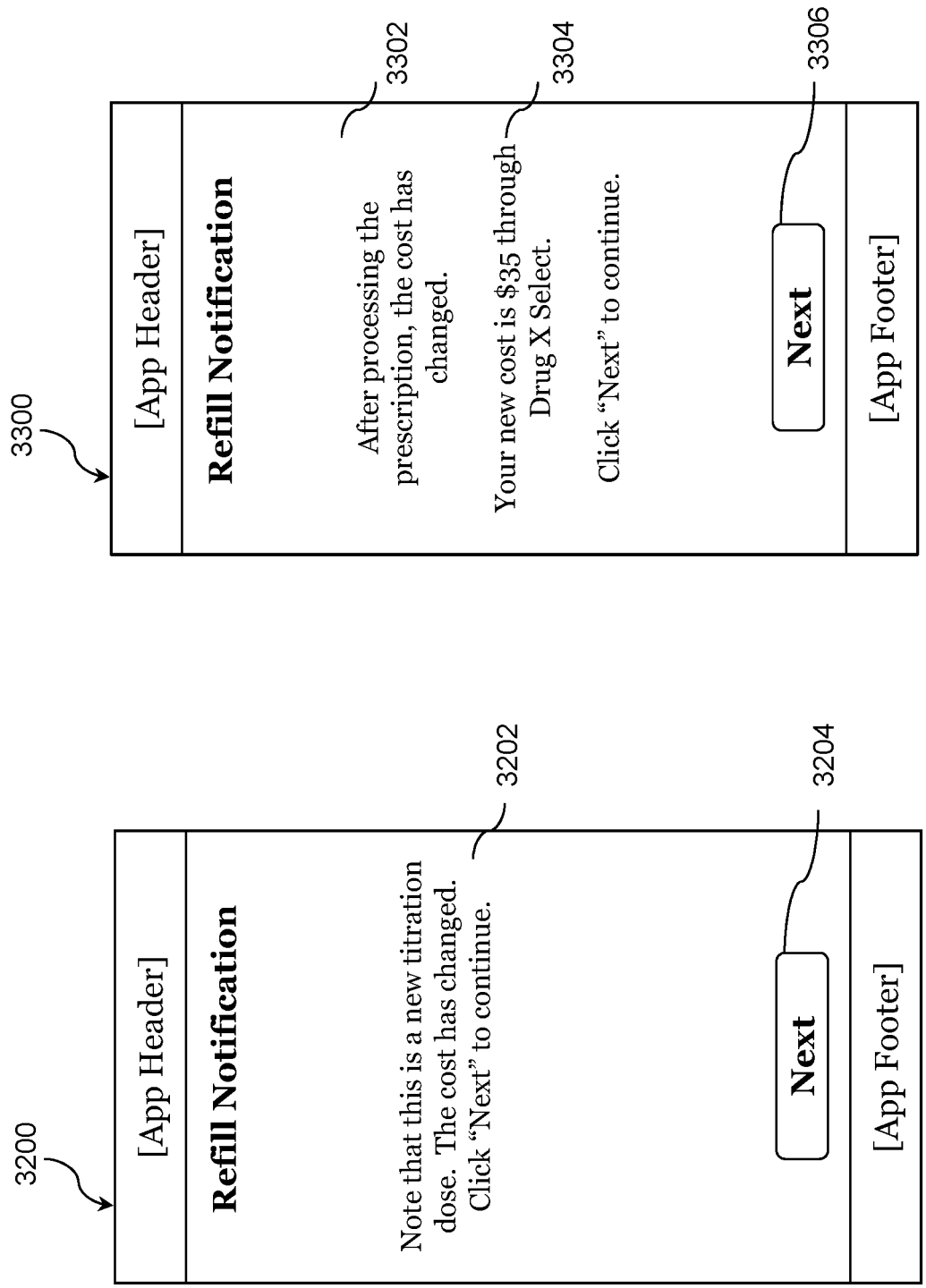

PRESCRIPTION DRUG FULFILLMENT SYSTEM AND METHOD

CROSS-REFERENCE TO RELATED APPLICATIONS

This application claims the benefit of priority to U.S. Provisional Patent Application Ser. No. 62/830,905, filed Apr. 8, 2019, entitled "PRESCRIPTION DRUG FULFILLMENT SYSTEM AND METHOD," the entire contents and disclosures of which are hereby incorporated by reference in their entirety.

FIELD OF USE

The disclosed subject matter relates to prescription fulfillment systems, and more specifically, to prescription fulfillment systems that enable a patient to electronically have a prescription fulfilled in an accurate, non-intrusive, and cost-effective manner.

BACKGROUND

In at least some known prescription fulfillment systems, patients prescribed a prescription drug may pay for the prescription drug i) by paying a co-pay or out-of-pocket amount that covers a portion of the total price of the prescription drug (referred to herein as an 'insured cost' for the prescription), with an insurance company paying the remainder of the total price or ii) by paying for the total price of the prescription drug without involving the insurance company (referred to herein as a 'non-insured cost' for the prescription). However, in at least some known prescription fulfillment systems, the patient may be unaware of the price difference between the insured and non-insured costs, and as a result may end up paying the more expensive of the two costs. Further, the patient may not be aware of the specific details of their insurance plan benefits (e.g. costs covered, restrictions, etc.). Furthermore, information about a patient's insurance plan as it relates to their prescription may be difficult to ascertain, especially from pharmacies. For example, the insured cost of the prescription may change in refilling the prescription due to the specific coverage details of the insurance plan, and the patient may be unaware of that change until they have to pay the cost for the refilled prescription.

Further, in at least some known prescription fulfillment systems, a physician may prescribe a first prescription drug and submit that prescription to a pharmacy. Although the prescription is written for the first prescription drug, in some circumstances, the pharmacy may substitute a second prescription drug (e.g., a generic version of the first prescription drug) for the first prescription drug without the patient's or the physician's knowledge. However, the second prescription drug may not be as efficacious for the patient. For example, some pharmacies may have an incentive to substitute the second prescription drug (e.g., the generic) due to state pharmacy mandates and/or based on other incentives.

In addition, in at least some known prescription fulfillment systems, when a patient has a prescription fulfilled at a brick and mortar pharmacy, several interactions (e.g., phone calls, in-person visits) may be required between the pharmacy and the patient before the prescription is filled. For example, the pharmacy may separately contact the patient to obtain insurance details to determine the insured cost, to inform the patient of the determined insured cost, and to inform the patient that the prescription drug is ready for pickup. These interactions may be time-consuming and intrusive to the patient, and may require the patient to be physically present at the pharmacy. Accordingly, in some situations, these interactions may cause delayed patient treatment and also may cause the patient to decide to forgo treatment and not to obtain the prescription drug. Additionally, pharmacies may not have an active prescription indicated on a patient's record, and therefore may not be proactive in filling refills of the prescription. Further, brick and mortar pharmacies may run out of medications that need to be filled, leaving patients without their prescription for days.

Further, at least some known prescription fulfillment systems allow patients to have a prescription drug directed mailed to them (e.g., "direct to patient pharmacies"). However, such direct to patient pharmacies, similar to brick and mortar pharmacies, also may require several interactions between the pharmacy and the patient. In addition, at least some known direct to patient pharmacies can only fill prescriptions with the patient paying the full, non-insured cost, and are unable to fill prescriptions paid for by both the patient (paying the insured cost) and the insurance company.

Additionally, at least some known prescription fulfillment systems allow patients to compare prices of a particular drug between different pharmacies. However, these known prescription fulfillment systems do not allow patients to compare non-insured and insured costs of the particular drug at a particular pharmacy. Further, these known prescription fulfillment systems simply allow the patient to compare the drug prices, and do not process the prescription for the patient.

BRIEF DESCRIPTION OF THE DISCLOSURE

In one aspect, a system for fulfilling a prescription of a prescription product for a patient covered by an insurance provider is provided. The system includes at least one processor in communication with at least one memory device. The at least one processor is programmed to (i) receive a prescription request including patient data relating to the patient, (ii) determine the insurance provider of the patient based on the received patient data, (iii) determine an insured cost for the prescription for the patient, wherein the insured cost is a cost the patient will pay for the prescription when a claim is filed with the determined insurance provider, (iv) determine a non-insured cost for the prescription for the patient, wherein the non-insured cost is a cost the patient will pay for the prescription without the claim being filed, (iv) compare the insured cost to the non-insured cost to determine which cost is lower, (v) if the insured cost is lower, a) transmit a message to the patient including a recommendation that an insurance claim be filed for the prescription, a first payment transaction request prompting the patient to enter payment details for the insured cost, and an authorization prompt for the patient to authorize the filing of the insurance claim and a first payment transaction for the insured cost, and b) process the insurance claim and the first payment transaction upon authorization by the patient, (vi) if the non-insured cost is lower, a) transmit a message to the patient including a recommendation that the patient pay the non-insured cost for the prescription and a second payment transaction request prompting the patient to enter payment details for the non-insured cost and authorize a second payment transaction for the non-insured cost, and b) process the second payment transaction upon authorization by the patient, and (vii) transmit the prescription to a pharmacy for further processing.

In another aspect, a computer-implemented method for fulfilling a prescription for a patient covered by an insurance provider is provided. The method includes (i) receiving a prescription request including patient data relating to the patient, (ii) determining the insurance provider of the patient based on the received patient data, (iii) determining an insured cost for the prescription for the patient, wherein the insured cost is a cost the patient will pay for the prescription when a claim is filed with the determined insurance provider, (iv) determining a non-insured cost for the prescription for the patient, wherein the non-insured cost is a cost the patient will pay for the prescription without the claim being filed, (v) comparing the insured cost to the non-insured cost to determine which cost is lower, (vi) if the insured cost is lower, a) transmitting a message to the patient including a recommendation that an insurance claim be filed for the prescription, a first payment transaction request prompting the patient to enter payment details for the insured cost, and an authorization prompt for the patient to authorize the filing of the insurance claim and a first payment transaction for the insured cost, and b) processing the insurance claim and the first payment transaction upon authorization by the patient, (vii) if the non-insured cost is lower, a) transmitting a message to the patient including a recommendation that the patient pay the non-insured cost for the prescription and a second payment transaction request prompting the patient to enter payment details for the non-insured cost and authorize a second payment transaction for the non-insured cost, and b) processing the second payment transaction upon authorization by the patient, and (viii) transmitting the prescription to a pharmacy for further processing.

In a further aspect, at least one non-transitory computer-readable media having computer-executable instructions thereon is provided. When executed by at least one processor of a prescription fulfillment system, the instructions may cause the at least one processor to (i) receive a prescription request including patient data relating to a patient, (ii) determine an insurance provider of the patient based on the received patient data, (iii) determine an insured cost for a prescription for the patient, wherein the insured cost is a cost the patient will pay for the prescription when a claim is filed with the determined insurance provider, (iv) determine a non-insured cost for a prescription for the patient, wherein the non-insured cost is a cost the patient will pay for the prescription without the claim being filed, (v) compare the insured cost to the non-insured cost to determine which cost is lower, (vi) if the insured cost is lower, a) transmit a message to the patient including a recommendation that an insurance claim be filed for the prescription, a first payment transaction request prompting the patient to enter payment details for the insured cost, and an authorization prompt for the patient to authorize the filing of the insurance claim and a first payment transaction for the insured cost, and b) process the insurance claim and first payment transaction upon authorization by the patient, (vii) if the non-insured cost is lower, a) transmit a message to the patient including a recommendation that the patient pay the non-insured cost for the prescription and a second payment transaction request prompting the patient to enter payment details for the non-insured cost and authorize a second payment transaction for the non-insured cost, and b) process the second payment transaction upon authorization by the patient, and (viii) transmit the prescription and one of the processed insurance claim and the processed payment transaction to a pharmacy for further processing.

BRIEF DESCRIPTION OF THE DRAWINGS

FIGS. 1-36 show example embodiments of the methods and systems described herein.

FIG. 1 illustrates a flow chart of an example embodiment of a prescription fulfillment system.

FIG. 2 illustrates a flow chart of an example embodiment of the prescription fulfillment system shown in FIG. 1 when fulfilling a refill prescription.

FIG. 3 is a simplified block diagram of an example prescription fulfillment system that includes computing devices in accordance with one example embodiment of the present disclosure.

FIG. 4 illustrates an example configuration of a client system shown in FIGS. 1 and 2.

FIG. 5 illustrates an example configuration of a server system shown in FIGS. 1 and 2.

FIG. 6 illustrates a diagram of components of one or more exemplary computing devices that may be used in one example embodiment of the present disclosure.

FIG. 7 illustrates an example data flow that may be used with the system shown in FIG. 1.

FIG. 8 is an example flow diagram for fulfilling a prescription.

FIG. 9 is an example flow diagram for fulfilling a refill prescription.

FIG. 10 illustrates a flow chart of an exemplary computer-implemented process for fulfilling a prescription as shown in FIG. 1.

FIGS. 11-36 are screenshots of one example of a patient application platform, as shown in FIG. 1.

Like numbers in the Figures indicate the same or functionally similar components.

DETAILED DESCRIPTION OF THE DISCLOSURE

Figure 1:
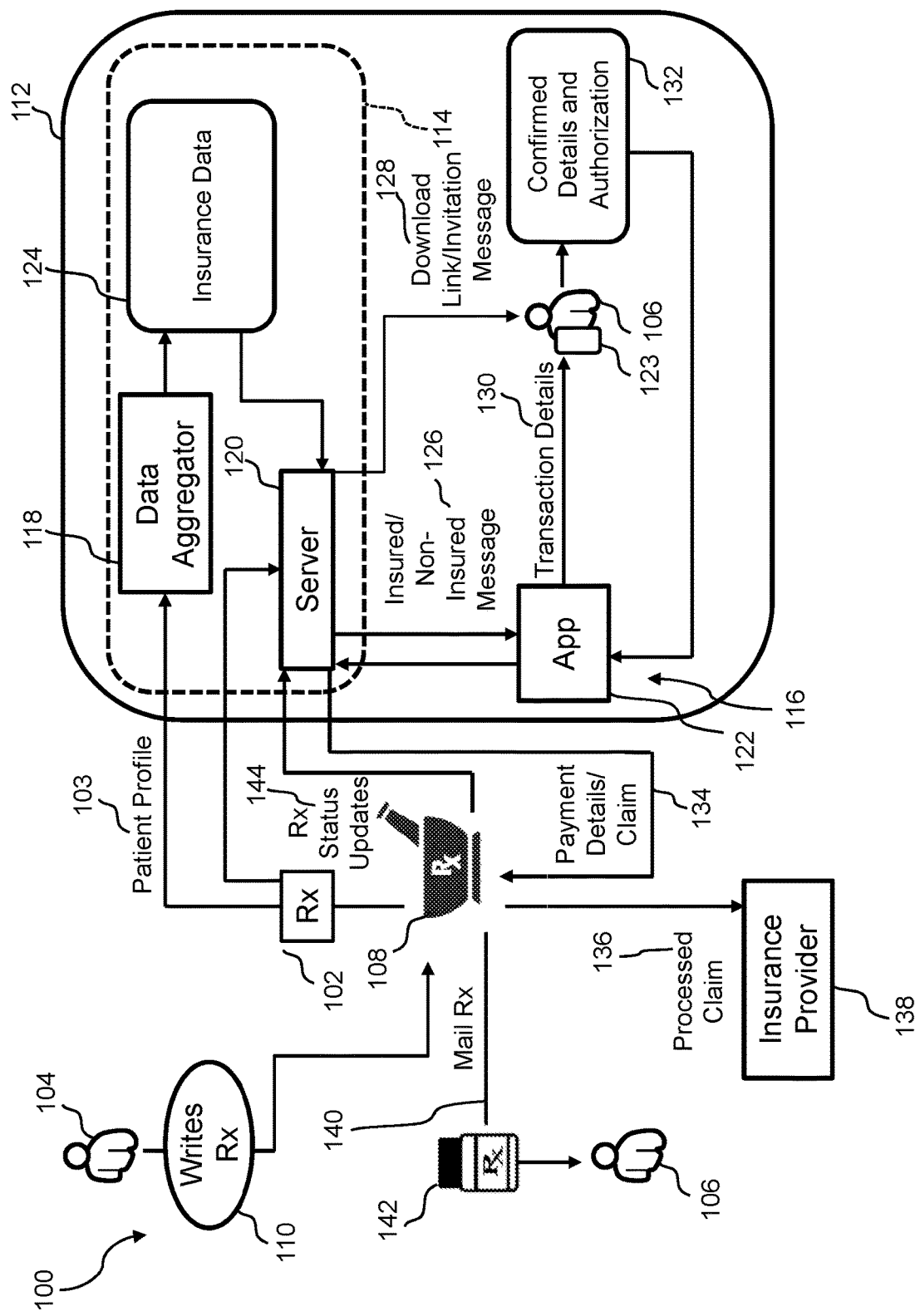

Embodiments of the methods and systems described herein enable determining a cost of a prescription for a user and accurately and non-intrusively fulfilling the prescription. For example, when a patient visits and consults with a healthcare provider (HCP) (e.g., a doctor, a nurse practitioner, or the like), the HCP may prescribe/order a product (e.g., a prescription medication) that must be fulfilled by a separate entity (e.g., a pharmacy). As used herein, the term prescription product may include drugs, pharmaceutical products, medical therapies, digital health therapeutics, digital health solutions, as well as any other products or procedures that require a prescription from an HCP. The embodiments disclosed herein also provide a patient application (e.g., executable on a mobile computing device) that facilitates comparing prescription prices and ensures that the patient pays the lowest cost of the insured cost and the non-insured cost for the prescription at a particular pharmacy.

The systems and methods described herein facilitate seamlessly fulfilling a prescription (e.g., through a pharmacy) prescribed to a patient by a HCP through a prescription fulfillment system. The prescription fulfillment system (i) determines patient information (e.g., insurance provider and plan information), (ii) compares an insured cost for the prescription based on the determined insurance information (e.g., the cost that the patient has to pay for the prescription when filing a claim with their insurance provider) to a non-insured cost of the prescription (e.g., the cost that the patient has to pay for the prescription without filing a claim), (iii) determines which cost is lower for the patient, (iv) provides an application for the patient to complete the transaction using the lower cost option, and (v) communicates transaction details to a pharmacy for the prescription to be fulfilled. The patient may enroll in the prescription fulfillment system through their HCP or independently.

At least one of the technical problems addressed by the systems and methods described herein includes: (i) inability to seamlessly fulfill a prescription through a comprehensive system; (ii) inability to rapidly retrieve and compare prescription prices (e.g., the price of a prescription with and without filing an insurance claim); (iii) lack of a direct-to-patient system for fulfilling prescriptions that handles both insurance claims and non-insured payments; (iv) lack of a system for fulfilling prescriptions that ensures that the patient is getting the exact prescription prescribed to them (e.g., in at least some known systems, the pharmacy may substitute a generic prescription without notifying the patient); and (v) requiring multiple interactions between patients, pharmacies, and insurance providers to process and complete an order for a prescription. Certain embodiments described herein may address one or more of these technical problems in a prompt, relatively automated fashion.

The methods and systems described herein may be implemented using computer programming or engineering techniques including computer software, firmware, hardware, or any combination or subset thereof, wherein the technical effects may be achieved by performing at least one of the following steps: (i) receiving a prescription request including patient data relating to the patient, (ii) determining the insurance provider of the patient based on the received patient data, (iii) determining an insured cost for the prescription for the patient, wherein the insured cost is a cost the patient will pay for the prescription when a claim is filed with the determined insurance provider, (iv) determining an non-insured cost for the prescription for the patient, wherein the non-insured cost is a cost the patient will pay for the prescription without the claim being filed, (v) comparing the insured cost to the non-insured cost to determine which cost is lower, (vi) if the insured cost is lower, a) transmitting a message to the patient including a recommendation that an insurance claim be filed for the prescription, a first payment transaction request prompting the patient to enter payment details for the insured cost, and an authorization prompt for the patient to authorize the filing of the insurance claim and a first payment transaction for the insured cost, and b) processing the insurance claim and the first payment transaction upon authorization by the patient, (vii) if the non-insured cost is lower, a) transmitting a message to the patient including a recommendation that the patient pay the non-insured cost for the prescription and a second payment transaction request prompting the patient to enter payment details for the non-insured cost and authorize a second payment transaction for the non-insured cost, and b) processing the second payment transaction upon authorization by the patient, and (viii) transmitting the prescription to a pharmacy for further processing.

The resulting technical effect achieved by the systems and methods described herein may include at least one of: (i) seamlessly fulfilling a prescription through a comprehensive system; (ii) providing an application that compares prescription prices (e.g., the price of a prescription with and without filing an insurance claim); (iii) providing a direct-to-patient system for fulfilling prescriptions that can handle both insurance claims and non-insured payments; and (iv) providing a direct-to-patient system for fulfilling prescriptions that ensures that the patient is getting the exact prescription prescribed to them.

For example, the prescription fulfillment system described herein includes a data aggregator that retrieves and aggregates insurance data (e.g., from insurance provider databases) and a server. To rapidly and accurately determine the price of a prescription when filing an insurance claim, the server compares patient identification information with the aggregated insurance data. Alternatively, a pharmacy may process a test claim (e.g., through a pharmacy management system associated with the pharmacy) to determine the price of the prescription using insurance, and communicate that determined price directly to prescription fulfillment system for further processing.

Further, the server of the prescription fulfillment system has access to a database including the price of a prescription when not filing an insurance claim. Advantageously, the price stored in the database may account for coupons, rebates, etc. to accurately reflect the actual price when not filing an insurance claim (as opposed to the listed retail price). Given the architecture of the prescription fulfillment system, the server of the system is uniquely positioned to rapidly determine an insured cost and a non-insured cost for a prescription, automatically compare the insured and non-insured costs, and enable the patient to rapidly and easily complete an order for the prescription at the lower of the insured and non-insured costs.

Specifically, the prescription fulfillment system described herein interfaces with a patient's mobile device (e.g., via an application) to process the order for the prescription using the insured or non-insured cost as appropriate. In the embodiments described herein, the application provides a dynamic user interface (described in detail below) that walks the patient through filling the prescription. For example, the patient is able to view the insured and non-insured costs, select which option they would like to use to purchase the prescription, and quickly input payment and shipping information to complete the order for the prescription. The user interface guides the patient through these steps through straight-forward and intuitive prompts, as described herein. The application may also, in some embodiments, aggregate data from a plurality of patients using the application and apply predictive modeling to the aggregated data to make real-time recommendations to a particular patient (e.g., recommending the insured or the non-insured cost).

In the embodiments described herein, the server of the prescription fulfillment system processes the prescription order using the information collected using the application operating on the patient's mobile device. For example, when the patient selects to purchase the prescription at the insured cost, the server may automatically complete and submit insurance claim forms to the appropriate insurance provider to initiate claim adjudication. Further, whether the patient selects to purchase the prescription at the insured or non-insured cost, the server may transmit the payment and shipping information to the pharmacy for the pharmacy to process payment and ship the prescription. Further, the application enables the patient to easily track the status of the prescription order. Thus, using the prescription fulfillment system described herein, all information necessary for prescription to be fulfilled is rapidly collected and transmitted to the pharmacy and/or the insurance provider, as appropriate, greatly reducing the number of interactions between the patient, pharmacy, and insurance provider as compared to at least some known systems.

The following detailed description illustrates embodiments of the disclosure by way of example and not by way of limitation. It is contemplated that the embodiments have general application to fulfilling prescriptions in a variety of applications.

As used herein, the term "database" may refer to either a body of data, a relational database management system (RDBMS), or to both. As used herein, a database may include any collection of data including hierarchical databases, relational databases, flat file databases, object-relational databases, object-oriented databases, and any other structured collection of records or data that is stored in a computer system. The above examples are example only and thus are not intended to limit in any way the definition and/or meaning of the term database. Examples of RDBMS's include, but are not limited to including, Oracle® Database, MySQL, Teradata, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one embodiment, a computer program is provided, and the program is embodied on a computer-readable medium. In an example embodiment, the system is executed on a single computer system, without requiring a connection to a sever computer. In a further embodiment, the system is being run in a Windows® environment (Windows is a registered trademark of Microsoft Corporation, Redmond, Wash.). In a further embodiment, the system is being run in an Apple® iOS environment (Apple is a registered trademark of Apple Inc., Cupertino, Calif.). In a further embodiment, the system is being run in a Google® environment (Google is a registered trademark of Google LLC, Mountain View, Calif.). In yet another embodiment, the system is run on a mainframe environment and a UNIX® server environment (UNIX is a registered trademark of X/Open Company Limited Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium.

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The embodiments described herein may be used to fill a prescription for any suitable drug. For example, the drug may be SYNTHROID (levothyroxine).

FIG. 1 is a flow chart of an example embodiment of a process 100 for fulfilling a prescription 102. In the exemplary embodiment, prescription 102 is prescribed by a healthcare provider (HCP) 104 for a patient 106. Further, prescription 102 is filled by a pharmacy 108.

In the exemplary embodiment, HCP 104 introduces patient 106 to a prescription fulfillment system 112, determines whether patient 106 would like prescription 102 to be processed by prescription fulfillment system 112, and writes 110 prescription 102 for patient 106. Prescription 102 is sent to pharmacy 108, and in the exemplary embodiment, prescription 102 includes patient identification information. Patient identification information may include a name, address, birthdate, phone number, and/or other identifying information for patient 106. In the exemplary embodiment, prescription 102 is an electronic prescription. That is, prescription 102 is electronically sent to pharmacy 108 by HCP 104 (e.g., through a computing device of HCP 104). In other embodiments, prescription 102 may be a written prescription that has to be physically sent to pharmacy 108. In the exemplary embodiment, once pharmacy 108 receives prescription 102, pharmacy 108 creates a patient profile 103 for patient 106. Pharmacy 108 sends prescription 102 and patient profile 103 to prescription fulfillment system 112 for processing. Specifically, pharmacy 108 sends the exact prescription 102 from HCP 104 to prescription fulfillment system 112 for processing. That is, pharmacy 108 does not process prescription 102 (e.g., pharmacy 108 does not determine the cost of prescription 102 or communicate with patient 106 for insurance and/or personal details). Accordingly, pharmacy 108 is unable to change and/or substitute prescription 102 for a different prescription (e.g., a generic of prescription 102) like in known systems, described above.

In some embodiments, pharmacy 108 manually runs prescription 112 through its own pharmacy management system (e.g., not immediately through prescription fulfillment system 112) or runs a test claim through prescription fulfillment system 112 to determine a cost of prescription 102 using insurance (e.g., the insured cost). That is, in some embodiments, pharmacy 108 runs a test claim through its system or through prescription fulfillment system 112 solely to determine the insured cost of prescription 102 and without actually fulfilling prescription 102. In these embodiments, pharmacy 108 may transmit the determined insured cost to prescription fulfillment system 112 such that patient 106 and/or prescription fulfillment system 112 can determine whether the insured cost or the non-insured cost is more economical for prescription 102, as described herein.

In the exemplary embodiment, prescription fulfillment system 112 includes a back-end 114 and a front-end 116. Patient 106 interacts with front-end 116 and does not access back-end 114. Back-end 114 includes a data aggregator 118 and a server 120. Front-end 116 includes an application, or app 122 that may be installed on a mobile device 123 of patient 106.

In the exemplary embodiment, data aggregator 118 collects data, including insurance data 124, from a variety of data sources. Insurance data 124 may include respective insurance providers, insurance plans, and insurance benefits for respective patients. In the exemplary embodiment, data aggregator 118 collects insurance data 124 without insurance providers being actively involved. That is, data aggregators 118 may have access to databases of insurance providers and may collect insurance data 124 freely from those databases without the insurance providers being made aware of the particular prescription. Insurance data 124 is sent from data aggregator 118 to server 120. Server 120 compares patient identification information from prescription 102 to insurance data 124 from data aggregator 118 to determine the specific insurance data 124 for patient 106. For example, server 120 may compare insurance data 124 associated with a specific patient (e.g., with a specific name, birthdate, and address) with the patient identification data included in prescription 102 to determine specific insurance data 124 for patient 106. Further, server 120 determines a non-insured cost and an insured cost (e.g., an out of pocket (OOP) cost) for patient 106 for prescription 102. The non-insured cost may be stored in server 120 and is a cost of prescription 102 for patient 106 when patient 106 does not file an insurance claim to pay for prescription 102. The non-insured cost may account for coupons, rebates, and discounts for prescription 106 that may be provided by a manufacturer of prescription 102. For example, a prescription 102 that costs $65 may have a non-insured cost of $25 after a $40 coupon is applied to the cost of prescription 102. The insured cost is determined by server 120 using determined insurance data 124 for patient 106. Specifically, the insured cost is the cost of prescription 102 for patient 106 based on the determined insurance plan when a claim is filed with the determined insurance provider. For example, a prescription 102 that costs $65 may have an insured cost of $25 for patient 106 when a claim is filed with their insurance provider (and the insurance provider pays $40). In another example, a prescription 102 that costs $65 may have an insured cost of $25 for patient 106 when a claim is filed with their insurance provider, the insurance provider pays $35, and a $5 coupon (e.g., co-pay assistance) is applied to the insured cost of prescription 102.

In the exemplary embodiment, server 120 compares the determined non-insured cost and determined insured cost to determine which cost is lower for prescription 102 for patient 106. Unlike known systems described above, server 120 ensures that patient 106 is paying the lowest possible cost for prescription 102 by comparing the non-insured and insured costs. Based on whether the non-insured cost or insured cost is lower, an insured or non-insured message 126 is sent to app 122. That is, if the non-insured cost is lower than the insured cost, a non-insured message 126 is sent to app 122, and if the insured cost is lower than the non-insured cost, an insured message 126 is sent to app 122. Message 126 may include a recommendation for patient 106 to pay with the insured or non-insured cost, as appropriate. Server 120 sends a message 128 including a download link and/or an invitation code to mobile device 123 of patient 106. Message 126 may include a link to download app 122 and an invitation code that links patient 106 to their determined insurance data 124 for app 122. Message 126 may further include determined insurance data 124 and the patient identification data from prescription 102.

Once patient 106 downloads app 122 and app 122 is initialized, app 122 displays prescription transaction details 130 to patient 106. Transaction details 130 may include determined insurance data 124, determined patient data, and message 126 that corresponds to a non-insured transaction or an insurance transaction. Patient 106 reviews and/or edits transaction details 130 on mobile device 123 and authorizes app 122 to fulfill prescription 102. Patient 106 may input payment information (e.g., credit/debit card information, Apple/Google Pay ID, PayPal information, etc.) to app 122 for the non-insured cost or insured cost of prescription 102. That is, confirmed transaction details and authorization 132 are input by patient 106 into app 122 and transmitted onto server 120.

In some embodiments, app 122 may further be configured to provide patient 106 with real-time suggestions built upon data from all patients 106 using app 122 and predictive modelling. That is, app 122 gathers data from patients 106 who use app 122 and can predict patient 106 behavior based on the gathered data. For example, app 122 may predict that most patients within a demographic similar to patient 106 usually pay the non-insured cost for prescription 102, and adjust its recommendations accordingly (e.g., app 122 may display the non-insured cost more prominently and/or display that most patients pay the non-insured cost when the non-insured cost is displayed). Further, app 122 may further be configured to provide support for patient 106 during their titration period (e.g., finding the right dosage of prescription 102 for patient 106 through trial and error) and may include a function that tracks symptom relief. App 122 may also be configured to engage and motivate patient 106 to remain compliant with prescription 102 and also may provide training information (e.g. videos, tutorials) on how to administer the prescription 102. For example, app 122 may send reminders to patient 106 to take their prescription at a certain time every day. Further, app 122 may remind patient 106 to remain complaint with HCP visits and also allow patients to connect with and interact with other patients taking the prescription 102 which may also increase patient compliance and/or adherence. App 122 may also be configured to offer financial incentives to patient 106, which may include, for example, variable pricing for prescription 102 and copay assistance for HCP 104 for patient 106.

In some embodiments, app 122 may further be configured to identify and display utilization management controls that affect patient 106. Utilization management controls include, for example, controls set in place by HCP 104, insurance provider 138, and/or pharmacy benefit managers within healthcare systems to keep healthcare costs low. For example, a utilization management control that affects patient 106 may be that their health insurance provider offers a very low insured cost for the first filling of prescription 102 and then raises the insured cost for patient 106 when prescription 102 is refilled. App 122 may notify patient 106 of the insured cost raise and/or instruct patient 106 to pay the non-insured cost for prescription 102 as soon as they are prescribed prescription 102 from HCP 104.

In the exemplary embodiment, server 120 processes payment information and/or an insurance claim for prescription 102. Specifically, in processing payment information, server 120 uses the payment information entered by patient 106 and processes the payment accordingly (e.g., charging a credit/debit card, deducting funds from a PayPal account, withdrawing funds from a healthcare savings account, etc.). When patient 106 pays the non-insured cost, server 120 processes the payment transaction without filing an insurance claim or interacting with an insurance provider 138. In processing insurance claims, server 120 may complete claim paperwork for the determined insurance provider of patient 106, communicate directly with the determined insurance provider to identify whether prescription 106 is covered by the provider, the cost of coverage, and any other conditions such as utilization management controls, and/or prepare the insurance claim for filing with the insurance provider. Payment details and/or insurance claims 134 are sent to pharmacy 108 for processing so that pharmacy 108 may start filling prescription 102 for patient 106. In an example embodiment, pharmacy 108 may send a processed claim 136 to insurance provider 138 as it is filling prescription 102. That is, in an example embodiment, prescription fulfillment system 112 initiates claim 136 adjudication and payment processing, but pharmacy 108 and/or a pharmacy management system associated with pharmacy 108 completes the claims adjudication and payment processing. In other embodiments, server 120 may send processed claim 136 to insurance provider 138 as server 120 sends processed claim 136 to pharmacy 108. Accordingly, based on a single selection by patient 106 in app 122 (i.e., "one-click"), all information (e.g., confirmed details and authorization 132) of patient 106 necessary for prescription 102 to be fulfilled is sent to server 120 and then pharmacy 108 and/or insurance provider 138, as appropriate. Thus, prescription fulfillment system 112 greatly reduces the number of interactions between patient 106 and HCP 104, pharmacy 108, and insurance provider 138.

In the exemplary embodiment, pharmacy 108 is a direct-to-patient pharmacy. That is, pharmacy 108 processes payment details and/or insurance claims 134, fills prescription 102, and mails 140 a filled prescription 142 to patient 106 without patient 106 having to directly interact with pharmacy 108 and/or go to a physical pharmacy location. Patient 106 receives prescription 102 with little to no contact with pharmacy 108, unlike known systems described above where many interactions between pharmacy 108 and patient 106 are required before patient 106 receives prescription 102. In other embodiments, pharmacy 108 may have a brick and mortar location, and patient 106 may have to pick up filled prescription 142 from the brick and mortar location. In an example embodiment, pharmacy 108 sends server 120 prescription filling status updates 144. Server 120 then sends status updates 144 to app 122, and app 122 displays status updates 144 to patient 106. Status updates 144 may include notifying patient 106 that prescription 102 has been received by pharmacy 108, that prescription 102 is being filled by pharmacy 108, that filled prescription 142 is being mailed by pharmacy 108, and mailing details (e.g., tracking number, estimated arrival time, etc.) of filled prescription 142. In other embodiments, pharmacy 108 may send status updates 144 directly to patient 106.

Figure 2:
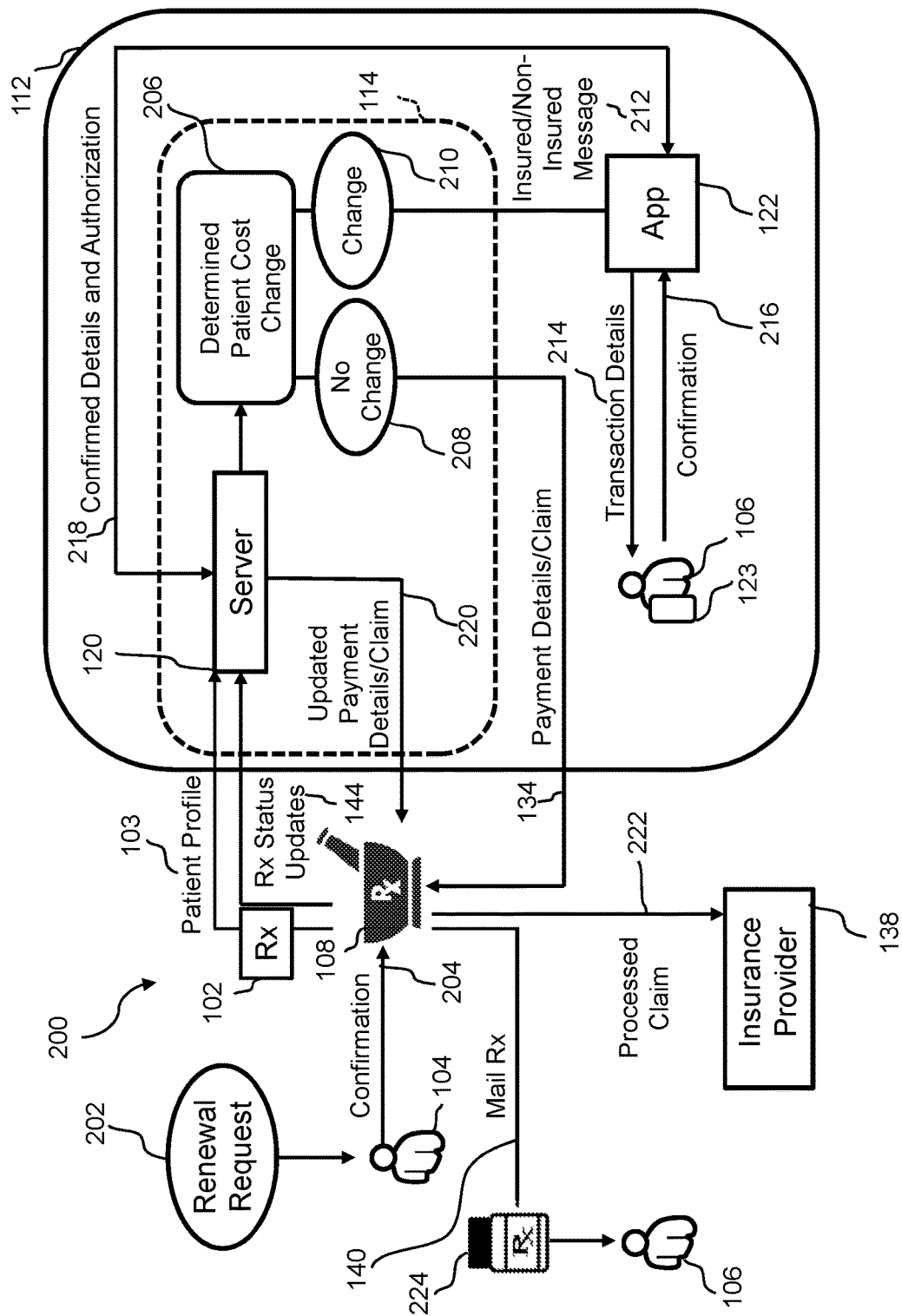

FIG. 2 is a flow chart of an example embodiment of a process 200 for renewing a previously filled prescription 102. In the exemplary embodiment, a renewal request 202 to refill prescription 102 is sent to HCP 104.

In the exemplary embodiment, HCP 104 confirms renewal request 202 and sends a confirmation 204 to pharmacy 108. Pharmacy 108 then sends prescription 102 and patient profile 103 to prescription fulfillment system 112 for processing. As described above with respect to FIG. 1, server 120 determines the lowest cost for patient 106 for prescription 102. In the exemplary embodiment, server 120 compares a current determined cost for patient 106 to a previous cost for patient 106 to determine 206 if the cost for patient 106 has changed. If there is no change 208 in the cost, payment details and/or insurance claims 134 are sent to pharmacy 108, and prescription 102 is filled in substantially the same way as described with respect to FIG. 1. If there is a change 210 in the cost (e.g., patient 106 reaches an insurance deductible, a new year starts so the insurance deductible must be reached again, patient 106 gets new insurance, coupons/rebates/discounts are discontinued, coupons/rebates/discounts are higher, etc.), the prescription 102 transaction is reauthorized and confirmed by patient 106.

Once patient 106 authorizes and confirms the change of cost in prescription 102, the filling of a refill prescription 102 is substantially similar to the filling of prescription 102, as described in FIG. 1. In the exemplary embodiment, a new insured/non-insured message 212 is sent to app 122. App 122 then displays new transaction details 214 on mobile device 123 of patient 106, and patient 106 inputs a confirmation 216 of transaction details 214 into app 122 on mobile device 123. Confirmed details and authorization 218 are sent to server 120, and updated payment details and/or insurance claims 220 are sent to pharmacy 108. Pharmacy 108 sends a new processed claim 222 to insurance provider 138. Further, pharmacy 108 mails 140 filled refill prescription 224 to patient 106 and may send prescription status updates 144 to patient 106 via app 122.

Figure 3:
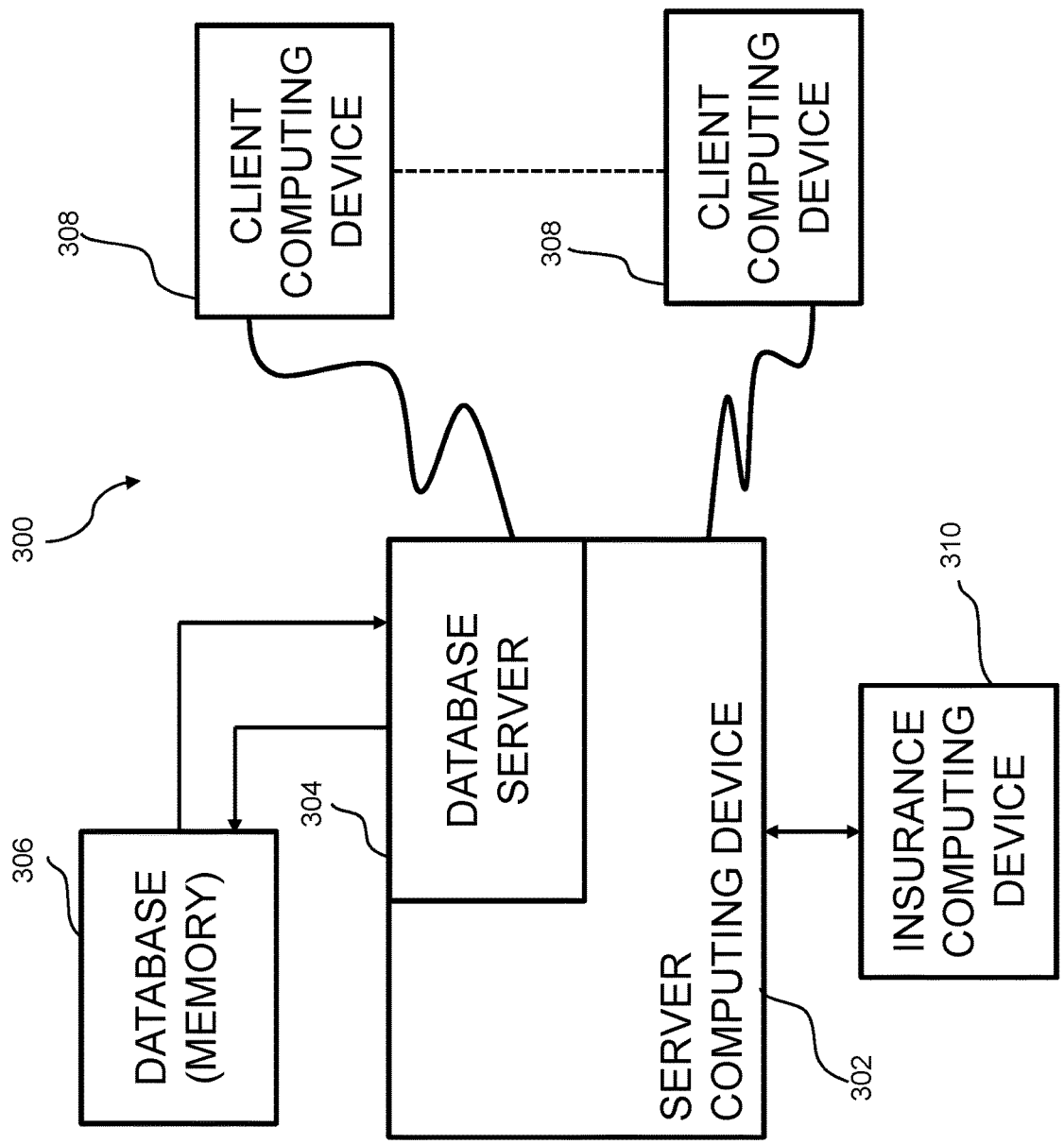

FIG. 3 is a simplified block diagram of one embodiment of a prescription fulfillment system 300 that includes a server system 302. Server system 302 includes a database server 304 and a database 306 in communication with server system 302. In some embodiments, server system 302 may be similar to server 120 (shown in FIG. 1), and database 306 may be associated with data aggregator 118 (shown in FIG. 1) and/or may store insurance data 124 (shown in FIG. 1) and transaction details 130 (shown in FIG. 1). System 300 further includes a plurality of client subsystems, also referred to as client systems 308 or client computing devices, connected to server system 302. In some embodiments, client systems 308 may be similar to mobile device 123 of patient 106 (shown in FIG. 1). Further, client systems 308 may be computing devices of healthcare providers 104 (shown in FIG. 1) and/or computing devices of pharmacy 108 (shown in FIG. 1). In one embodiment, client systems 308 are computers including a web browser, such that server system 302 is accessible to client systems 308 using the Internet or another network. Client systems 308 are interconnected to the Internet or another network through many interfaces including a network, such as a local area network (LAN) and/or a wide area network (WAN), dial-in connections, cable modems, wireless-connections, and special high-speed ISDN lines. Client systems 308 may be any device capable of interconnecting to the Internet including a web-based phone, personal digital assistant (PDA), watch, medical device, kiosk, laptop computer, desktop computer, netbook, tablet, phablet, or other web-connectable equipment. System 300 further includes an insurance system 310 or insurance computing device in communication with server system 302. In some embodiments, insurance system 310 may be associated with insurance provider 138 (shown in FIG. 1).

Database server 304 is connected to database 306 containing information on a variety of matters, as described herein in greater detail. In one embodiment, database 306 is stored on server system 302 and may be accessed by potential users at one of client systems 308 by logging onto server system 302 through one of client systems 308. In an alternative embodiment, database 306 is stored remotely from server system 302 and may be non-centralized (e.g., in a cloud computing configuration). Server system 302 could be any type of computing device configured to perform the steps described herein. As described herein, server system 302 collects and stores data from a plurality of data sources in database 306 and distributes the data to client systems 308 and insurance system 310 to fulfill a prescription.

Figure 4:
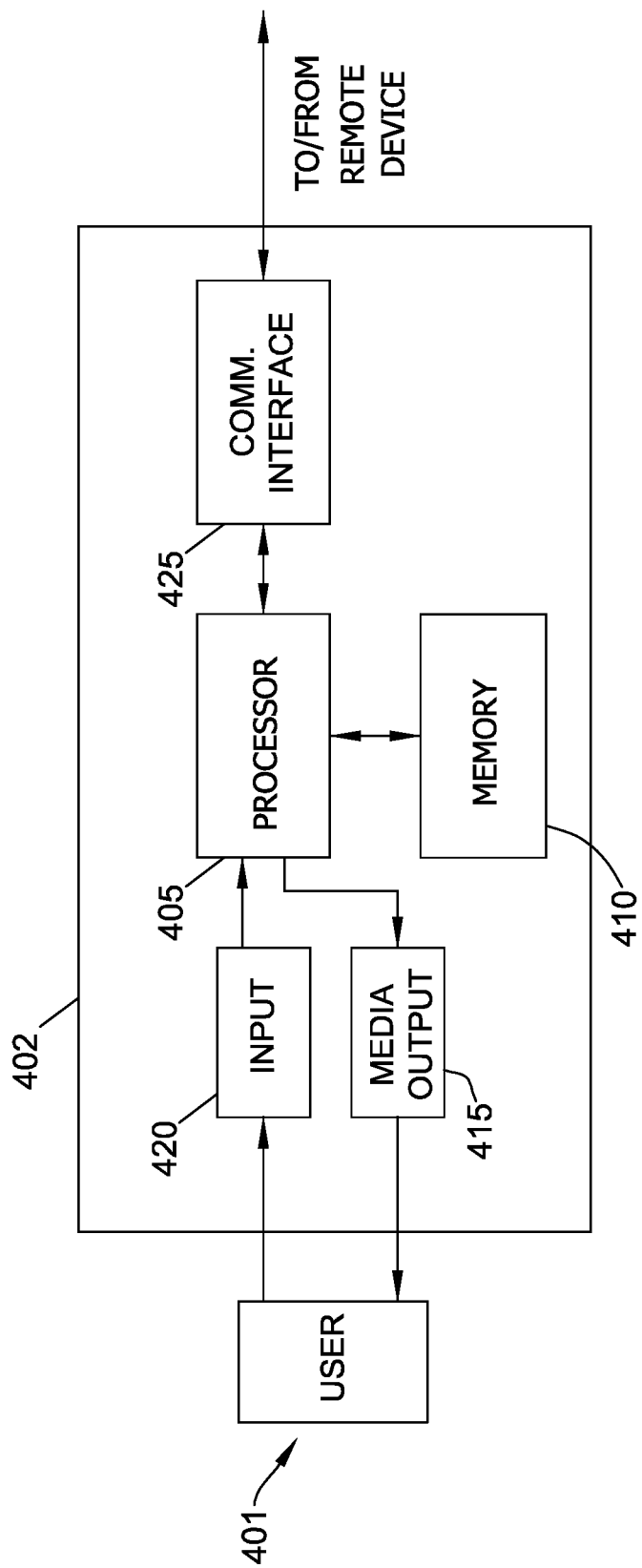

FIG. 4 illustrates an example configuration of a user computing device 402 operated by a user 401. In some embodiments, user 401 may be HCP 104 and/or patient 106 (shown in FIG. 1). User computing device 402 may include, but is not limited to, mobile device 123 (shown in FIG. 1) and client systems 308 (shown in FIG. 3).

User computing device 402 includes one or more processors 405 for executing instructions. In some embodiments, executable instructions are stored on one or more memory devices 410. Processor 405 may include one or more processing units (e.g., in a multi-core configuration). One or more memory devices 410 are any one or more devices allowing information such as executable instructions and/or other data to be stored and retrieved. One or more memory devices 410 may include one or more computer-readable media.

User computing device 402 also includes at least one media output component 415 for presenting information to user 401. Media output component 415 is any component capable of conveying information to user 401. In some embodiments, media output component 415 includes an output adapter such as a video adapter and/or an audio adapter. An output adapter is operatively coupled to processor 405 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, user computing device 402 includes an input device 420 for receiving input from user 401. Input device 420 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 415 and input device 420.

User computing device 402 may also include a communication interface 425, which is communicatively coupleable to a remote device such as server system 202. Communication interface 425 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in one or more memory devices 410 are, for example, computer-readable instructions for providing a user interface to user 401 via media output component 415 and, optionally, receiving and processing input from input device 420. A user interface may include, among other possibilities, a web browser and client application. Web browsers enable users, such as user 401, to display and interact with media and other information typically embedded on a web page or a website from server system 302 (shown in FIG. 3). A client application allows user 401 to interact with a server application from server system 302 or a web server.

Figure 5:
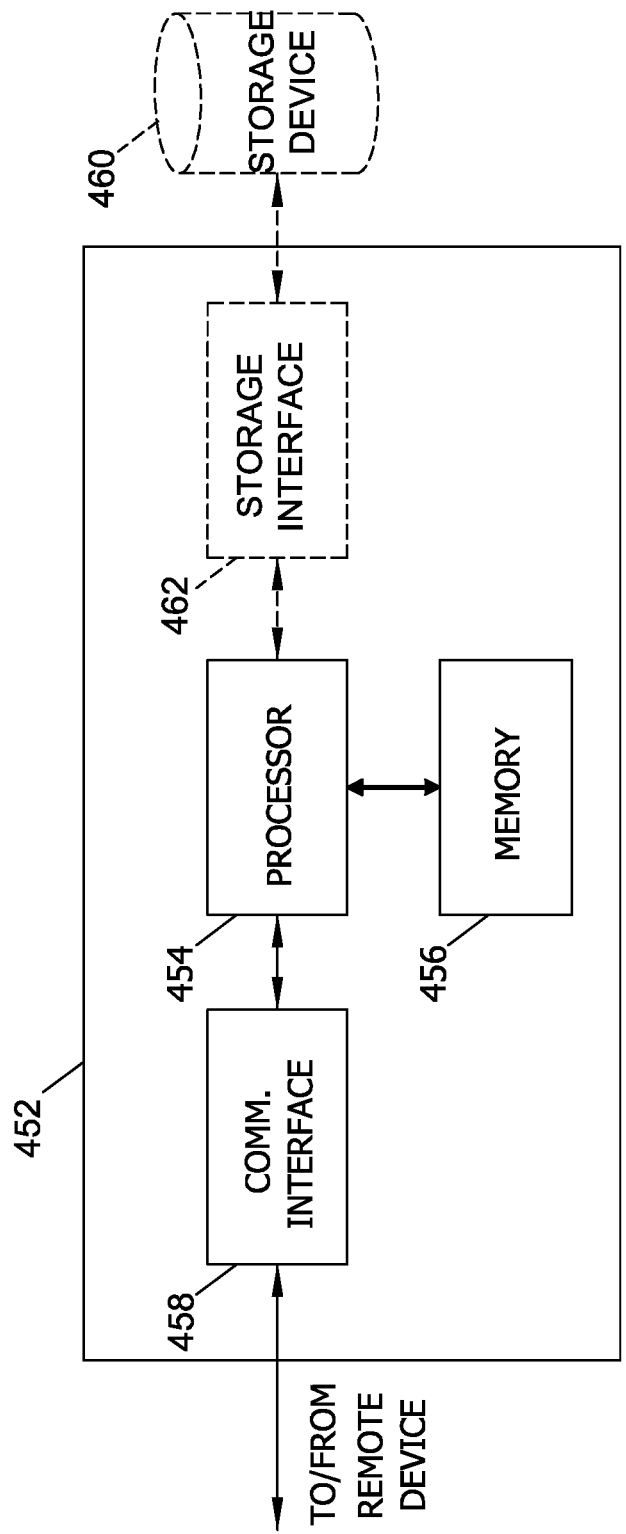

FIG. 5 illustrates an example configuration of a server computing device 452 such as server 120 (shown in FIGS. 1 and 2) and server system 302 (shown in FIG. 3). Server computing device 452 may include, but is not limited to, database server 304. Server computing device 452 is also representative of insurance computing device 310 (shown in FIG. 3).

Server computing device 452 includes one or more processors 454 for executing instructions. Instructions may be stored in one or more memory devices 456, for example. One or more processors 454 may include one or more processing units (e.g., in a multi-core configuration).

One or more processors 454 are operatively coupled to a communication interface 458 such that server computing device 452 is capable of communicating with a remote device such as data source computing device 402 or another server computing device 452. For example, communication interface 458 may receive requests from client systems 308 via the Internet or another network, as illustrated in FIG. 3.

One or more processors 454 may also be operatively coupled to one or more storage devices 460. One or more storage devices 460 are any computer-operated hardware suitable for storing and/or retrieving data. In some embodiments, one or more storage devices 460 are integrated in server computing device 452. For example, server computing device 452 may include one or more hard disk drives as one or more storage devices 460. In other embodiments, one or more storage devices 460 are external to server computing device 452 and may be accessed by a plurality of server computing devices 452. For example, one or more storage devices 460 may include multiple storage units such as hard disks or solid state disks in a redundant array of inexpensive disks (RAID) configuration. One or more storage devices 460 may include a storage area network (SAN) and/or a network attached storage (NAS) system. In some embodiments, one or more storage devices 460 may include database 306 (shown in FIG. 3).

In some embodiments, one or more processors 454 are operatively coupled to one or more storage devices 460 via a storage interface 462. Storage interface 462 is any component capable of providing one or more processors 454 with access to one or more storage devices 460. Storage interface 462 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing one or more processors 454 with access to one or more storage devices 460.

One or more memory devices 410 and 456 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

Figure 6:
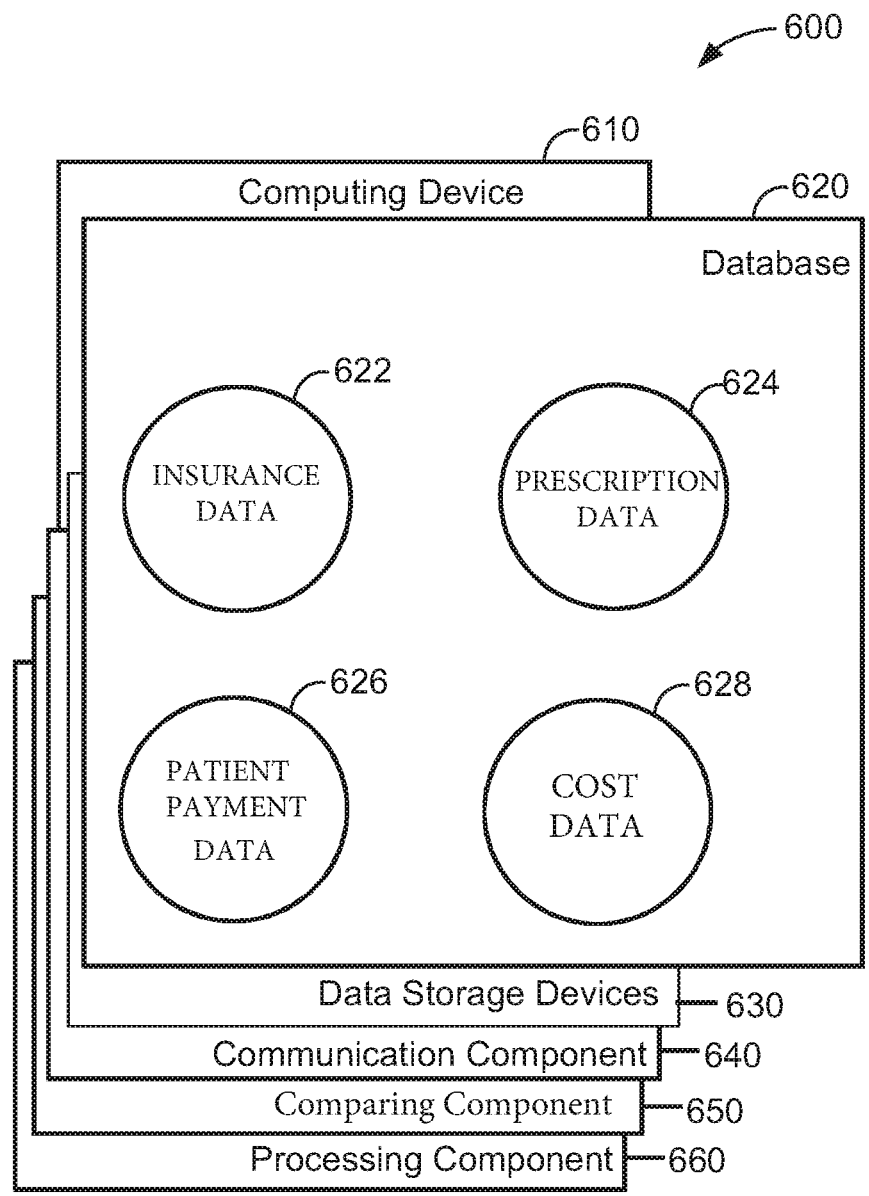

FIG. 6 depicts a diagram 600 of components of one or more exemplary computing devices 610 that may be used in process 100 (shown in FIG. 1), process 200 (shown in FIG. 2), and system 300 (shown in FIG. 3). In some embodiments, computing device 610 may be used to implement back-end 114 of prescription fulfillment system 112 (shown in FIG. 1) and/or server system 302 (shown in FIG. 3). Database 620 may be coupled with several separate components within computing device 610, which perform specific tasks. In this embodiment, database 620 may include insurance data 622 (which may be similar to insurance data 124 shown in FIG. 1), prescription data 624 (which may be related to prescription 102 shown in FIG. 1), patient/payment data 626 (which may be data and payment data, for example, payment card account details, online payment account details, etc., associated with patient 106 shown in FIG. 1), and cost data 628 (which may be associated with determined insurance and non-insured costs, as described with respect to FIG. 1). In some embodiments, database 620 is similar to database 306 (shown in FIG. 3)

Computing device 610 may include the database 620, as well as data storage devices 630. Computing device 610 may also include a communication component 640 for transmitting and receiving data between HCP 104, patient 106, pharmacy 108, back-end 114, app 122, and insurance provider 138 (all shown in FIG. 1). Computing device 610 may further include a comparing component 650 for determining if non-insured cost or Insured cost is lower. A processing component 660 may assist with execution of computer-executable instructions associated with the system, including processing insurance claims and prescription transactions.

Figure 7:
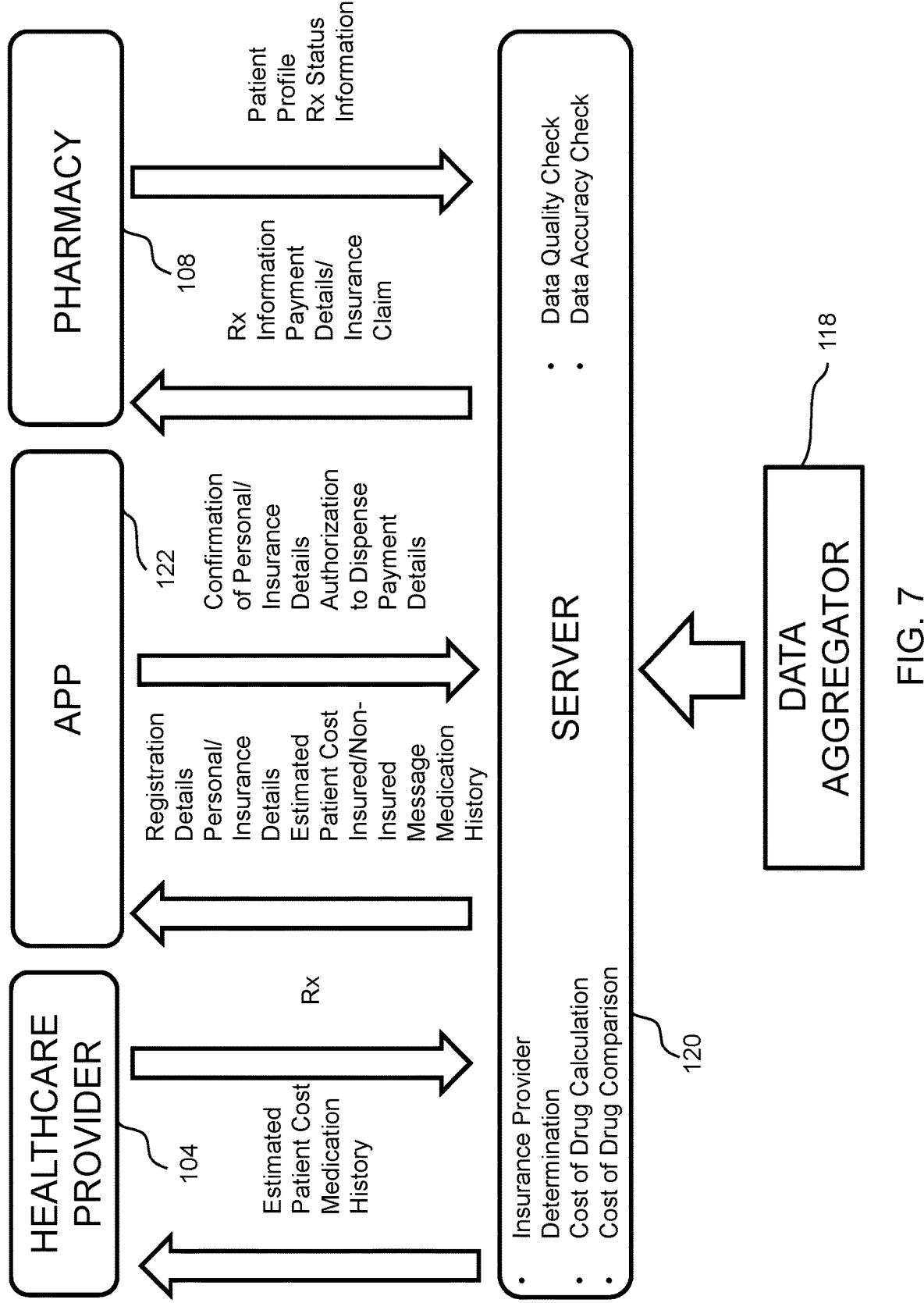

FIG. 7 illustrates an example data flow to and from various components in process 100 shown in FIG. 1. In the example embodiment, data aggregator 118 is a data platform that receives benefits data (e.g., prescription benefits data and/or medical benefits data) and medication history (e.g., fill history) data. This data may be received from insurance providers (like insurance provider 138 shown in FIG. 1), pharmacy benefits managers (PBMs) and/or other data sources. Data aggregator 118 may be a comprehensive report platform that provides a range of services, including a secure, reliable, scalable, and HIPAA compliant reports system. Data aggregator 118 determines pharmacy eligibility information, pharmacy benefits information, medical benefits information, and medication history information for patients. In the example embodiment, data aggregator 118 translates raw data from a source and delivers the data to various applications via server 120. The benefits data and medication history data may be provided in any suitable format.

Using data for a particular patient, server 120 may, for example, determine an insurance provider, calculate an insured and a non-insured drug cost for the patient, and compare the insured and non-insured drug costs, as described in detail above. The calculated drug costs may be determined in response to a prescription for a specific drug written for patient by HCP 104. The request may be a web-based request transmitted from a remote user computing device to server 120 over the Internet. Server 120 may also be configured to perform a data quality and a data accuracy check of the data of data aggregator 118 to check the data for inconsistencies and/or inaccuracies. For example, data received from data aggregator 118 may be checked for accuracy by comparing it against data previously stored by server 120. In another example, data received from data aggregator 118 may be checked to ensure it matches a desired format (e.g., ensuring a drug cost value is for a predetermined time interval, such as thirty days, and not for a different time interval, such as ninety days). Further, in addition to the functions described above, server may use machine learning techniques to compile metadata regarding coverage of a prescription product for different insurance companies.

Data generated by server 120 may then be provided to HCP 104, patient application 122, and/or pharmacy 108. For example, for a particular patient and prescription product, app 122 may receive and display patient registration details, patient personal and/or insurance details, a patient cost, a non-insured or insured message, and medication history. Additionally, data generated by HCP 104, app 122, and/or pharmacy 108 may provide server 120 with the generated data. For example, pharmacy 108 may provide server 120 with prescription status information. Server 120 may store the data and/or provide the received data to other users HCP 104, app 122, and/or pharmacy 108.

Figure 8:
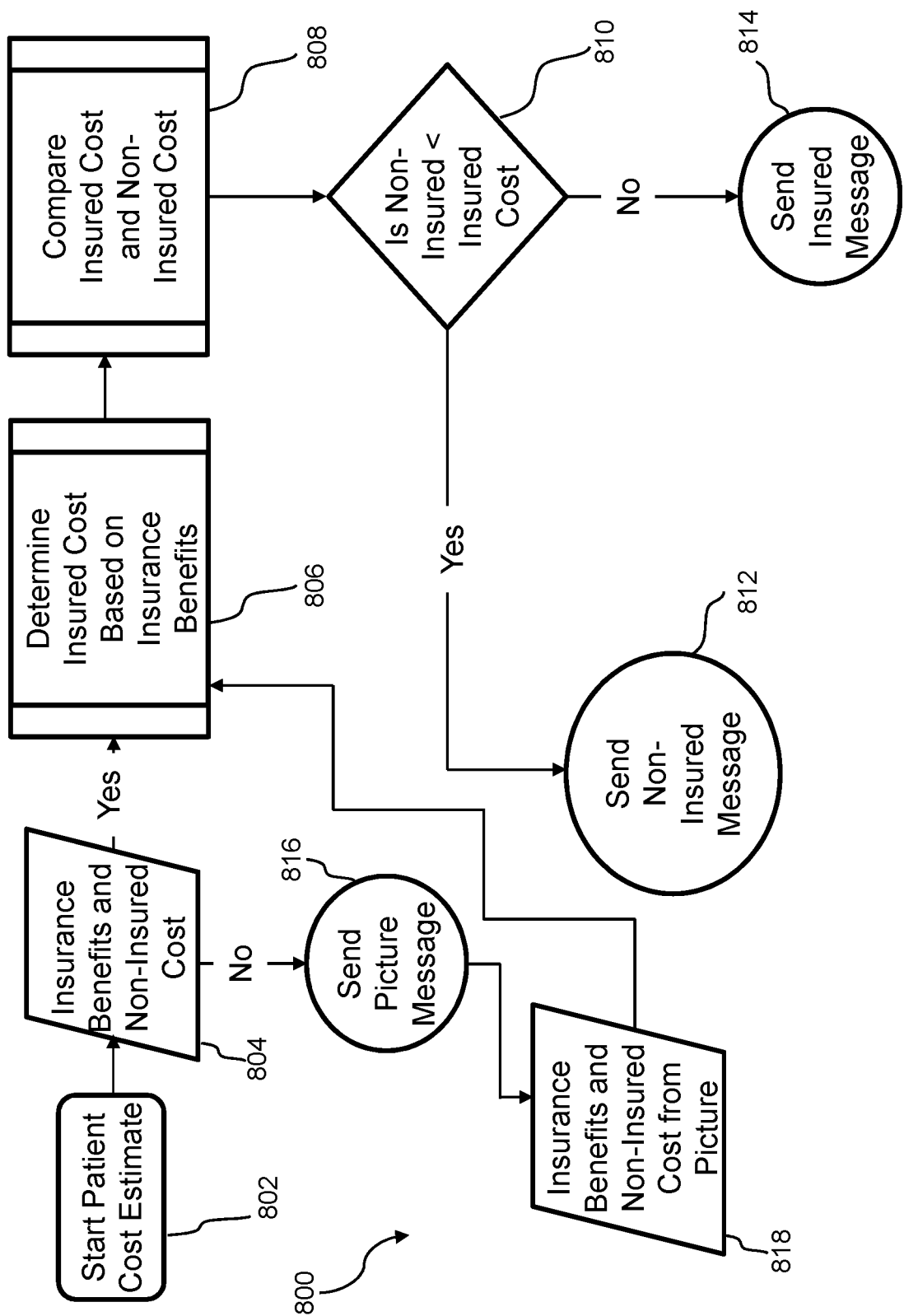

The following is an example of determining a payment method for a specific patient. FIG. 8 shows a flow diagram generally corresponding to process 100, illustrated in FIG. 1. The following steps are performed by server 120 (shown in FIG. 1) in the example embodiment. In response to a prescription from an HCP (e.g., HCP 104 shown in FIG. 1), a patient cost estimate is initiated 802, and server 120 receives 804 insurance benefits and non-insured cost from a data source (e.g., data aggregator 118 shown in FIG. 1).

If the insurance benefits are not received 804 because of insufficient insurance information, server 120 sends 816 an image request message to the patient. The image request message prompts the patient to acquire an image of their insurance and/or prescription card (e.g., using their mobile computing device). Then server 120 may determine 818 the insurance benefits and non-insured cost based on the image.

Next, server 120 determines 806 an insured cost based on the received 804 or determined 818 insurance benefits for the specific patient. Server 120 then compares 808 the determined insured cost and the received non-insured cost for the patient.

Next, server 120 determines 810 whether the received non-insured cost is less than the determined insured cost. If the non-insured cost is lower than the insured cost, server 120 sends 812 a non-insured message to app 122 (as shown and described in FIG. 1). If the non-insured cost is higher than the insured cost, server 120 sends 814 an insured message to app 122 (as shown and described in FIG. 1).

Figure 9:
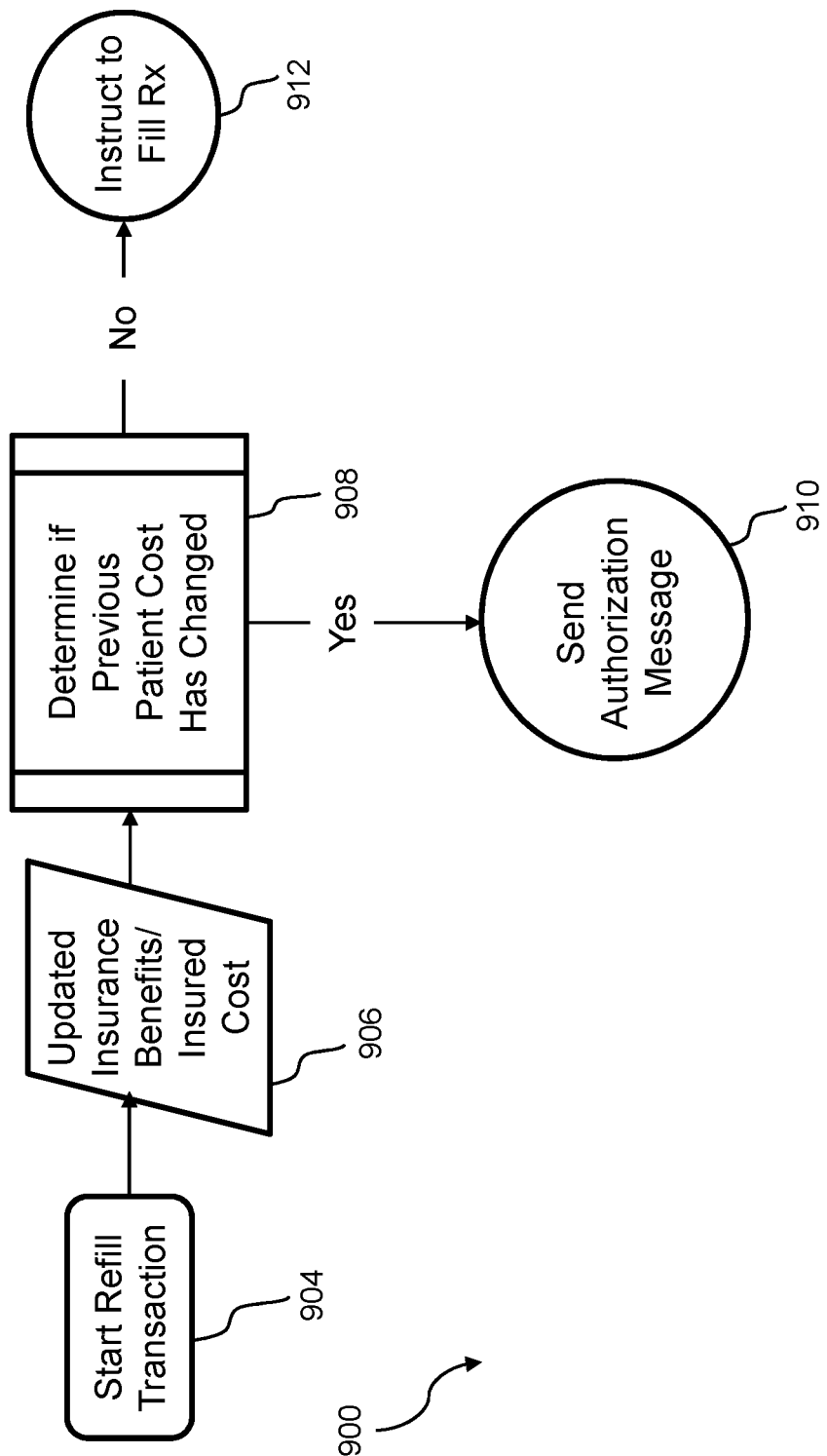

The following is an example of how a prescription refill is processed. FIG. 9 shows a flow diagram 900 generally corresponding to process 200, illustrated in FIG. 2. The following process is performed by server 120 (shown in FIG. 1) in the example embodiment. In response to a request for a refill, refill transaction is initiated 904 and any updated insurance benefits and/or non-insured cost are received 906 from a data source (e.g., data aggregator 118 shown in FIG. 1).

Next, server determines 908 if a previous patient cost has changed. If the previous patient cost has changed, server 120 sends 910 an authorization message to app 122 (as shown and described in FIG. 2). If the previous patient cost has not changed, server 120 instructs 912 a pharmacy to fill the prescription as it did previously (as shown and described in FIG. 2).

Figure 10:
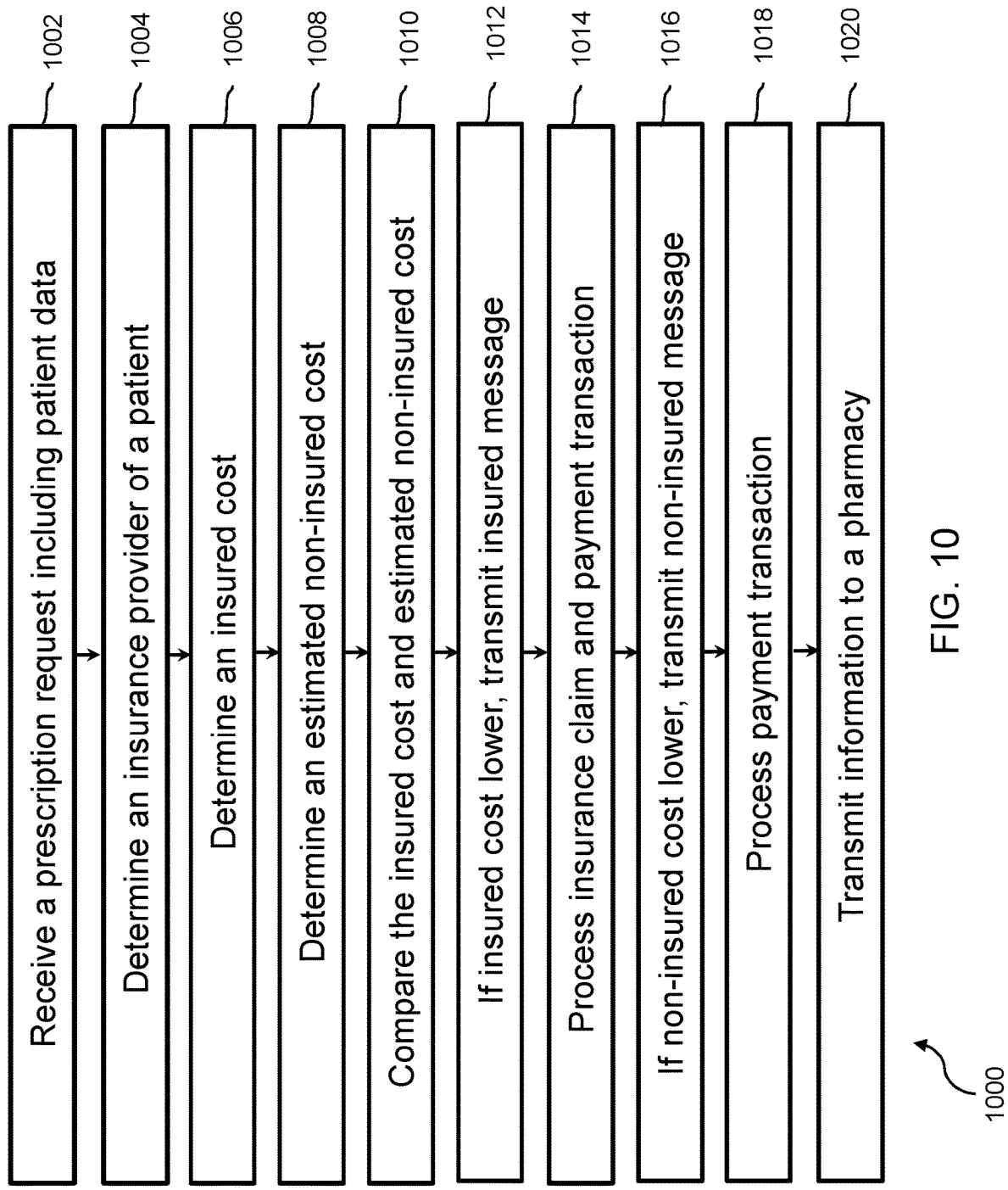

FIG. 10 illustrates a flow chart of an exemplary computer-implemented method 1000 for fulfilling a prescription. Method 1000 may be carried out by prescription fulfillment system 112 (shown in FIG. 1).

In the exemplary embodiment, method 1000 includes receiving 1002 a prescription request including patient data. This patient data may be received 1002 by server 120 (shown in FIG. 1) from data aggregator 118 (shown in FIG. 1). Further, method 1000 includes determining 1004 insurance data for a patient, determining 1006 a insured cost, and determining 1008 a non-insured cost based on the received 1002 patient data.

In the exemplary embodiment, method 1000 further includes comparing 1010 the insured cost and the non-insured cost. If the insured cost is lower, method 1000 includes sending 1012 an insured message and subsequently processing 1014 an insurance claim and payment transaction. If the non-insured cost is lower, method 1000 includes sending 1016 a non-insured message and processing 1018 a payment transaction. In either case, the messages may be sent 1012, 1016 to app 122 of mobile device 123 of patient 102.

Method 1000 further includes transmitting 1020 information to a pharmacy (e.g., pharmacy 108 shown in FIG. 1) for further processing. Transmitting 1020 information to the pharmacy may cause the pharmacy to send an insurance claim (e.g., insurance claim 136 shown in FIG. 1) to an insurance provider (e.g., insurance provider 138), mail a filled prescription (e.g., filled prescription 142) to the patient (e.g., patient 106), and/or provide the prescription fulfillment system with status updates (e.g., status updates 144) of the prescription.

FIGS. 11-36 include screenshots of one example embodiment of a patient application (e.g., "Drug X Select Program") as part of a prescription fulfillment system (e.g., prescription fulfillment system 112 shown in FIG. 1). For example, the patient application may be app 122 (shown in FIG. 1). The patient application may be accessible on any suitable electronic device, such as a mobile phone, tablet, watch, or any other computing device. The patient application enables a patient to log-in, see a determined lowest cost for a prescription (e.g., a prescription for "Drug X"), authorize the filling of the prescription, and provide payment details. In some embodiments, the patient application may enable the patient subscribe to medication reminders and/or updates via email, phone, and/or text.

The patient application may be configured to communicate with various other software and/or applications on the patient's computing device. For example, the patient application may be able to access or otherwise communicate with payment applications (e.g., Apple/Google Pay and/or PayPal) and/or calendar applications. The patient application may be configured to retrieve data from and/or report data to these other applications. In addition, the patient application may be configured to track, monitor, and/or record application utilization metrics for the patient, such as how often the patient accesses the patient application, and the various features of the patient application used by the patient.

In one embodiment, the patient application, once downloaded onto the patient's computing device, may not require internet connectivity to perform some or all of the functionality of the patient application (e.g., setting alerts and notifying the patient with those alerts). In some embodiments, all or a portion of the data input by the patient into the patient application (including, for example, application utilization metrics, refill logs, etc.) may be electronically transmitted to a server (e.g., server 120) for processing, and the processed data may be transmitted for further processing and/or display by the patient application.

FIG. 11 illustrates a text message screen 1100 including a first text message 1102 and a second text message 1104. Text message screen 1100 includes instructions for downloading the patient application and is therefore outside of the patient application. That is, text message screen 1100 is displayed on a mobile device of the patient prior to the patient downloading the patient application and is not part of the patient application itself. First text message 1102 includes a link 1106 for downloading the patient application. Second text message 1104 includes an invitation code 1108 that is specific to the patient and links the patient application to the personalized patient data. The text may be sent from a healthcare provider, a pharmacy, and/or a server of the prescription fulfillment device.

FIG. 12 illustrates a registration page 1200 for the patient application. Registration page 1200 includes a first field 1202 for the patient to enter their invitation code (e.g., invitation code 1108 from second text message 1104) and a second field 1204 for the patient to enter their date of birth. Registration page 1200 further includes a confirm button 1206 that may be distorted, grayed out, and/or unable to be clicked until the patient enters valid information into first and second fields 1202 and 1204. Once confirm button 1206 is clicked, the patient application displays a detail confirmation page 1400 as illustrated in FIG. 14.

The patient application includes an app header 1208 and an app footer 1210. Although not specifically shown, app header 1208 may include a home button, a back button, and any other buttons to help the patient navigate the patient application. Further, although not specifically shown, app footer 1210 may include a help button (e.g., that leads the patient to app support).

FIG. 13 illustrates an error page 1300 if the information provided by the patient in first and second fields 1202 and 1204 is invalid and/or incorrect. Error page 1300 includes an error message 1302 indicating that the patient's information could not be found. Error page 1300 also includes a resend code button 1304 that, when pressed by the patient, will resend invitation code 1108 via text message and start the patient over at the beginning of the registration process (e.g., text message screen 1100). Additionally or alternatively, error page 1300 includes a camera message 1306 indicating that the patient may share their information by taking a picture of their insurance/prescription card. Error page 1300 includes a camera button 1308 that, when pressed by the patient, will actuate the camera (not specifically shown) of the mobile device so that the patient may take a picture of their insurance/prescription card. Once the picture is taken, the patient application will continue the registration of the patient and displays detail confirmation page 1400 as illustrated in FIG. 14.

FIG. 14 illustrates detail confirmation page 1400 with a prompt 1402 instructing the patient to edit and confirm details. Detail confirmation page 1400 includes fields 1404, 1406, 1408, 1410, 1412, 1414, 1416, and 1418. In the example embodiment, fields 1404, 1406, 1408, 1410, 1412, 1414, 1416, and 1418 are pre-filled by the patient application based on the information provided by the patient entering invitation code 1108 into registration screen 1200. In other embodiments, fields 1404, 1406, 1408, 1410, 1412, 1414, 1416, and 1418 may be empty, requiring the patient to fill in each of fields 1404, 1406, 1408, 1410, 1412, 1414, 1416, and 1418. In the exemplary embodiment, a first field 1404 relates to patient first name, a second field 1406 relates to patient last name, a third field 1408 relates to patient date of birth, a fourth field 1410 relates to address line 1 of the address of the patient, a fifth field 1412 relates to address line 2 of the address of the patient, a sixth field 1414 relates to patient zip code, and a seventh field 1416 relates to patient state. In other embodiments, fields 1404, 1406, 1408, 1410, 1412, 1414, 1416, and 1418 may relate to any identifying patient information. The patient may edit any of fields 1404, 1406, 1408, 1410, 1412, 1414, 1416, and 1418 if the information is missing and/or incorrect. Once fields 1404, 1406, 1408, 1410, 1412, 1414, 1416, and 1418 are correctly filled, the patient may press a confirm button 1418 to cause the patient application to display an insurance details screen 1500 as illustrated in FIG. 15 or a terms of use screen 1600 as illustrated in FIG. 16.

FIG. 15 illustrates insurance details screen 1500. Like fields 1404, 1406, 1408, 1410, 1412, 1414, 1416, and 1418 of detail confirmation page 1400, a field 1502 may be already filled out by the patient application or the patient may need to fill out field 1502. In the exemplary embodiment, field 1502 is a picture of a health insurance card of the patient. If field 1502 is not automatically filled out by the patient application, field 1502 may prompt the patient to take a picture of their health insurance card and/or fill out the information from the health insurance card manually. Once field 1502 is filled out and correct, the patient may press a confirm button 1504 to cause the patient application to display terms of use screen 1600.

FIG. 16 illustrates terms of use screen 1600 that prompts users to read and accept terms of use. Terms of use screen 1600 includes a "Terms of Use" header 1602 and a message 1604 indicating the terms of use. Terms of use screen 1600 also includes an accept button 1606 that, when pressed by the patient, confirms that the patient has read and accepted the terms of use, and causes the patient application to display one of message screens 1700, 1800, 1900, 2000, 2100, 2200, 2300, and 2400.

Figure 25:
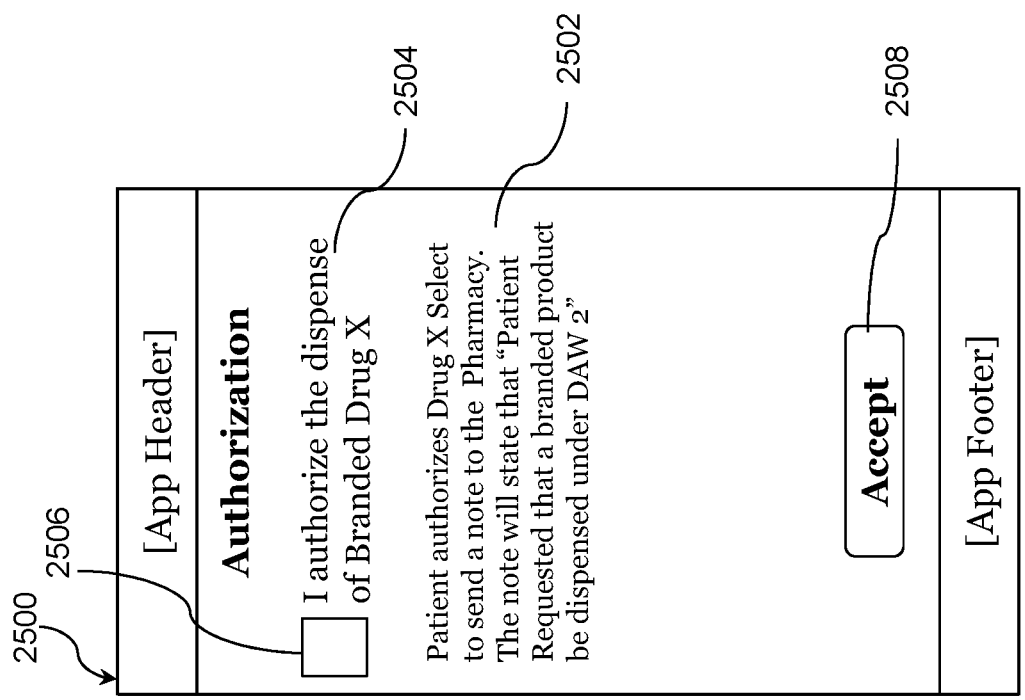

FIG. 17 illustrates a first message screen 1700. First message screen 1700 includes a message 1702 that informs the patient that their insurance covers Drug X for $25 for a 30 day supply. First message screen 1700 is shown to the patient when the insured cost is determined to be the lowest cost of Drug X for the patient, as described above in detail. First message screen 1700 includes a next button 1704 that causes the patient application to display an authorization screen 2500 as illustrated in FIG. 25.

FIG. 18 illustrates a second message screen 1800. Second message screen 1800 includes a first message 1802 that indicates insurance covers Drug X for $40 for a 30 day supply, and a message 1804 that Drug X Select offers Drug X for $35 for a 30 day supply. Messages 1802 and 1804 are shown to the patient when the non-insured cost is determined to be the lowest cost of Drug X for the patient, as described above in detail. Second message screen 1800 includes a next button 1806 that causes the patient application to display authorization screen 2500 illustrated in FIG. 25.

FIG. 19 illustrates a third message screen 1900. Third message screen 1900 includes a first message 1902 that insurance covers Drug X for $25 for a 30 day supply, a second message 1904 that the patient will be required to transition to a mandated pharmacy after a grace fill where Drug X will cost $40 for a 30 day supply, and a third message 1906 that Drug X is available through Drug X Select for $35 for a 30 day supply. Messages 1902, 1904, and 1906 are shown to the patient when it is determined that while the insured cost appears to be lower initially, it will cost more than the non-insured cost of Drug X over time. Message screen 1900 includes a next button 1908 that causes the patient application to display authorization screen 2500 illustrated in FIG. 25.

Figures 20, 21, 22:
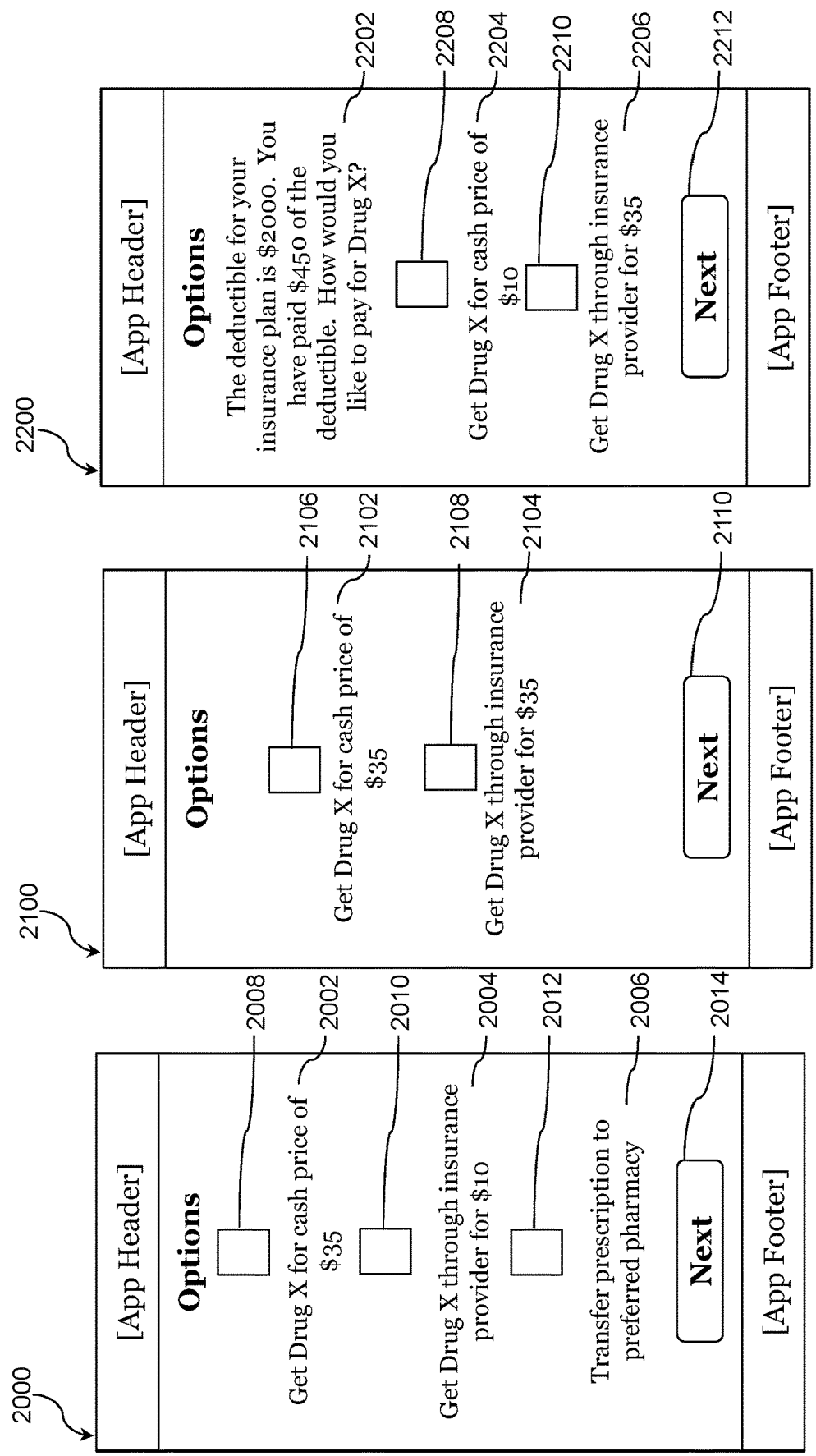

FIG. 20 illustrates a fourth message screen 2000 that includes options for the patient to choose from. Fourth message screen 2000 includes a first message 2002 that the patient can get Drug X for the cash price of $35, a second message 2004 that the patient can get Drug X through their insurance provider for $10, and a third message 2006 that the prescription can be transferred to the patient's preferred pharmacy. First message 2002 is accompanied by a first check box 2008, second message 2004 is accompanied by a second check box 2010, and third message 2006 is accompanied by a third check box 2012. When the patient decides which option contained in messages 2002, 2004, 2006 is the option they want to choose, they press the corresponding check box 2008, 2010, 2012. For example, if the patient wants their prescription transferred to their preferred pharmacy (e.g., the option contained in message 2006), the patient checks third check box 2012. Further, fourth message screen 2000 includes a next button 2014. Pressing the next button causes the patient application to display the next appropriate screen based on check box 2008, 2010, 2012 that was checked by the patient. Specifically, if first check box 2008 or second check box 2010 is checked by the patient, pressing the next button causes the patient application to display authorization screen 2500 illustrated in FIG. 25. If third check box 2012 is checked by the patient, pressing the next button may cause the patient application to display a message (not specifically shown) that the patient application has successfully transferred the prescription to the patient's preferred pharmacy.

FIG. 21 illustrates a fifth message screen 2100. Fifth message screen 2100 includes a first message 2102 that the patient can get Drug X for a cash price of $35 and a second message 2104 that the patient can get Drug X through their insurance provider for $35. That is, fifth message screen 2100 shows that the cash price (e.g., the non-insured cost) and the insured cost are the same. Accordingly, fifth message screen 2100 also includes a first check box 2106 that accompanies first message 2102 and a second check box 2108 that accompanies second message 2104. Once the patient decides which option contained in messages 2102 and 2104 is the option they wish to choose, they can select the corresponding check box 2106 or 2108. For example, if the patient wants to pay cash for the prescription (the option contained in first message 2102), they select check box 2106. Further, fifth message screen 2100 includes a next button 2110 that, when selected, causes the patient application to display authorization screen 2500 illustrated in FIG. 25.

FIG. 22 illustrates a sixth message screen 2200. Sixth message screen 2200 includes a first message 2202, a second message 2204, and a third message 2206. First message 2202 includes information about the patient's deductible and how much of the deductible the patient has paid. Second message 2204 includes that the patient can get Drug X for a cash price of $10, and third message 2206 includes that the patient can get Drug X through their insurance provider for $35. Second message 2204 is accompanied by a first check box 2208, and third message 2206 is accompanied by a second check box 2210. The information included in first message 2202 may come from a data aggregator (e.g., data aggregator 118, shown in FIG. 1) and may be included in the patient application to help the patient make an informed decision about their payment choice. For example, the cost included in second message 2204 is lower than the cost included in third message 2206, but the cost included in third message 2206 would be applied to the patient's deductible. Since first message 2202 includes information about the patient's deductible, the patient may decide that they will likely reach their deductible and choose to pay the cost included in third message 2206 even though the cost included in second message 2204 is cheaper initially. Other patients may decide that they will likely not reach their deductible and choose to pay the lower cost included in second message 2204. Sixth message screen 2200 also includes a next button 2212 that, when selected, causes the patient application to display authorization screen 2500.

In other embodiments, the patient application is only configured to accept cash payments and does not run any prescriptions through insurance. In these embodiments, the patient application displays confirmation page 1400. Subsequently, when confirm button 1418 is selected, the patient application displays terms of use screen 1600, and then, when accept button 1606 is selected, the patient application displays a seventh message screen 2300 as shown in FIG. 23. Seventh message screen 2300 includes a message 2302 that informs the patient of a price of Drug X for a predetermined formulation (Y mg) for a 30 day supply. Seventh message screen 2300 is shown to the patient when the lowest possible cash cost (e.g., including manufacturer coupons, etc.) is determined, as described above in more detail. Seventh message screen 2300 includes a next button 2304 that causes the patient application to display an eighth message screen 2400 as illustrated in FIG. 24 or authorization screen 2500.

FIG. 24 illustrates eighth message screen 2400 that includes options for the patient to choose from. Eighth message screen 2400 includes a first message 2402 that the patient can get Drug X for the cash price of $35 and a second message 2404 that the prescription can be transferred to the patient's preferred pharmacy. First message 2402 is accompanied by a first check box 2406, and second message 2404 is accompanied by a second check box 2408. When the patient decides which option contained in messages 2402, 2404 is the option they want to choose, they select the corresponding check box 2406, 2408. Further, eighth message screen 2400 includes a next button 2410. Pressing the next button causes the patient application to display the next appropriate screen based on the check box 2406 or 2408 that was checked by the patient. Specifically, if first check box 2406 is checked by the patient, selecting the next button causes the patient application to display authorization screen 2500 illustrated in FIG. 25. If second check box 2408 is checked by the patient, selecting the next button may cause the patient application to display a message (not specifically shown) that the patient application has successfully transferred the prescription to the patient's preferred pharmacy.

FIG. 25 illustrates authorization screen 2500. Authorization screen 2500 includes a message 2502, a statement 2504, and a check box 2506. Message 2502 includes an explanation that the patient authorizes the patient application to send a note to a pharmacy indicating that the prescription for the patient should be filled. Statement 2504 includes an explicit statement that the patient authorizes the dispense of Drug X accompanied by check box 2506. By checking check box 2506, the patient authorizes the dispensing of Drug X using the patient application. Authorization screen 2500 includes an accept button 2508 that causes the patient application to display a payment method screen 2600.

FIG. 26 illustrates payment method screen 2600. Payment method screen 2600 includes field 2602 for the patient to determine which payment method they want to use for the insured and/or non-insured cost for Drug X. For example, even though the patient pays the insured cost for Drug X, the patient may need to cover their out of pocket cost. In the exemplary embodiment, field 2602 may include, for example, Apple Pay, Visa, MasterCard, and debit as payment methods. In other embodiments, field 2602 may include PayPal account payments, Google Pay, and any other applicable payment method. The patient may select their payment method from field 2602 and hit a next button 2604 that causes the patient application to display a payment details screen 2700.

FIG. 27 illustrates payment details screen 2700. Payment details screen 2700 includes a field 2702 for the patient to fill out their payment details. In the example embodiment, field 2702 relates to credit card information. In other embodiments, field 2702 may relate to signing into an Apple Pay account and providing debit card information. The patient may hit a next button 2704 to cause the patient application to display a payment decline screen 2800 or a confirmation screen 2900.

FIG. 28 illustrates payment decline screen 2800. If the patient inputs invalid and/or incorrect information into payment details screen 2700, payment decline screen 2800 is displayed on the patient application. Payment decline screen 2800 includes a first message 2802 indicating that the payment information entered was declined. Payment decline screen 2800 also includes a next button 2804 that, when pressed, causes the patient application to display payment details screen 2800 so that the patient can correct the payment details.

Figure 29:
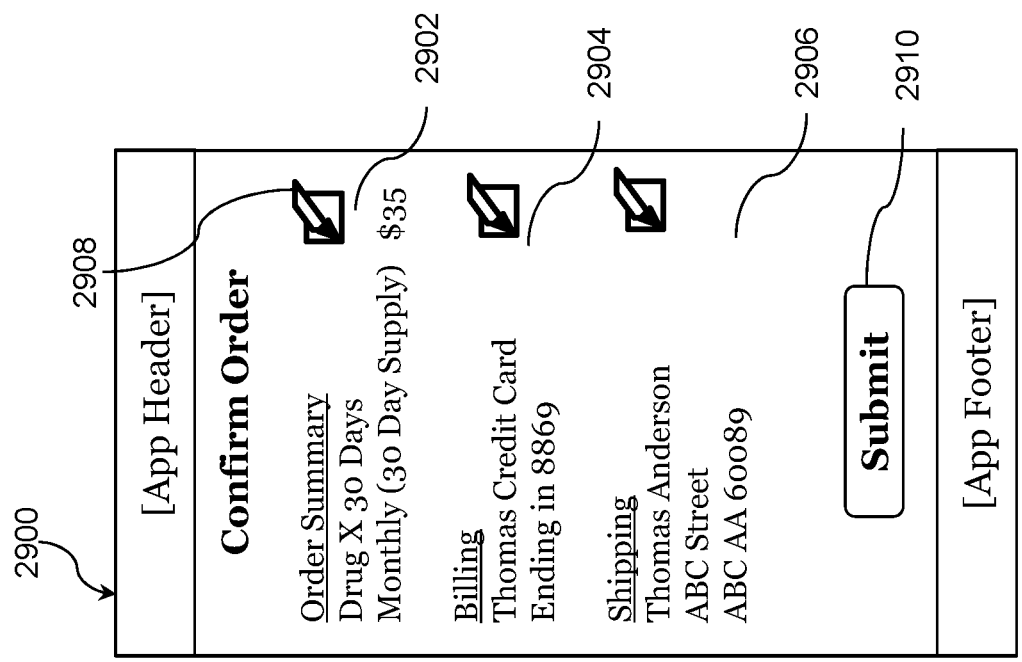

FIG. 29 illustrates confirmation screen 2900. If the payment details entered by the patient in payment details screen 2700 are approved, confirmation screen 2900 is displayed by the patient application. Confirmation screen 2900 includes fields 2902, 2904, and 2906. A first field 2902 includes Drug X information and cost information to be confirmed from one of message screens 1700, 1800, 1900, 2000, 2100, 2200, 2300, 2400. A second field 2904 includes billing information to be confirmed from payment details screen 2700. A third field 2906 includes shipping information to be confirmed from confirmation page 1400. Each of fields 2902, 2904, and 2906 is accompanied by an edit button 2908 that allows the patient needs to go back and update information in fields 2902, 2904, and 2906. If edit button 2908 is selected, the patient application will display one of respective screens 1400 and 2700 so that patient may edit the applicable fields. The patient may finalize the transaction by hitting a submit button 2910. Once the transaction is finalized, the patient application sends the transaction details to the pharmacy, as described above in further detail. In some embodiments, submit button 2910, when selected, causes the patient application to display a tracking screen 3000 or a current prescriptions screen 3100.

Figure 30:
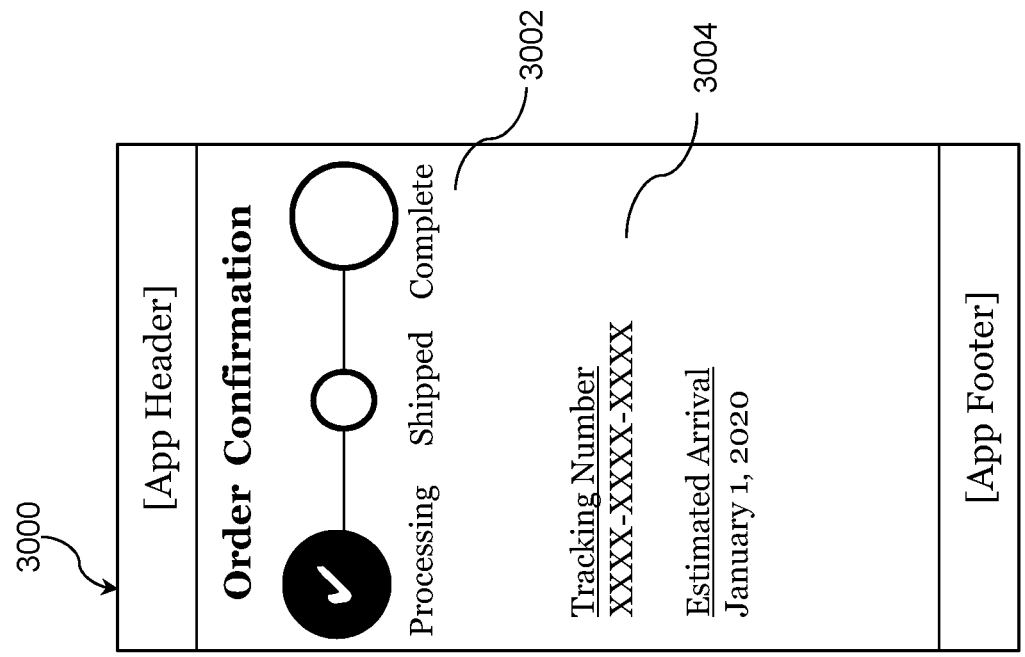

FIG. 30 illustrates tracking screen 3000. Tracking screen 3000 includes a status bar 3002 and a first message 3004. Status bar 3002 shows the status of the current prescription. For example, status bar 3002 may include a processing bubble, a shipping bubble, and a complete bubble. The processing bubble may be filled in once the current prescription order is submitted and being processed. The shipping bubble may be filled in once the current prescription order is shipped. The complete bubble may be filled in once the prescription has been delivered. First message 3004 includes additional order information including, for example, a shipping tracking number once the prescription has been shipped, an estimated delivery date once the prescription has been shipped, the delivery address, or any other information relating to the prescription order.

Figure 31:
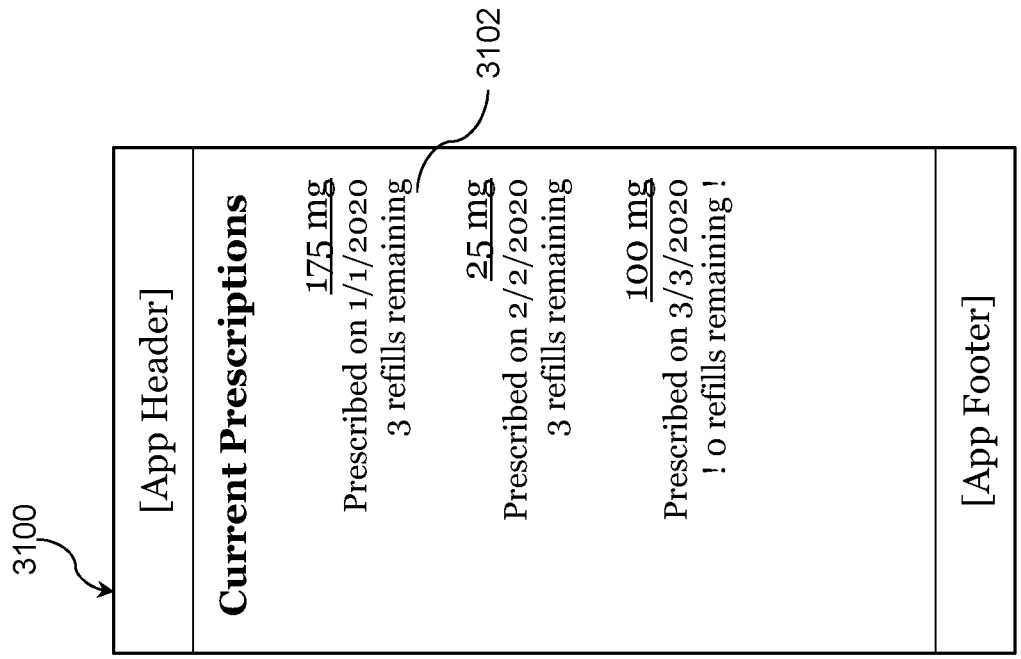

FIG. 31 illustrate current prescription screen 3100. Current prescription screen 3100 includes a message 3102 associated with multiple different prescriptions and the statuses of the different prescriptions. Message 3102 may include, for example, the prescriptions and the respective dosages of the prescriptions, a date when each prescription was prescribed, and how many refills are remaining for each prescription.

FIG. 32 illustrates a first refill message screen 3200. First refill message screen 3200 includes a message 3202 indicating that a refill of the patient's prescription is a new titration dose and that the cost has changed. First refill message screen 3200 includes a next button 3204 that, when selected, may cause the patient application to display any of message screens 1700, 1800, 1900, 2000, 2100, 2200, 2300, 2400, a second refill message screen 3300, a third refill message screen 3400, or a fourth refill message screen 3500.

FIG. 33 illustrates second refill message screen 3300. Second refill message screen 3300 includes a first message 3302 indicating that after processing the prescription, the cost of the prescription has changed, and a second message 3304 indicating that the new cost of Drug X is $35 through Drug X Select. Second refill message screen 3300 also includes a next button 3306 that, when selected, may cause the patient application to display authorization screen 2500, third refill message screen 3400, or fourth refill message screen 3500.

Figures 34, 35:
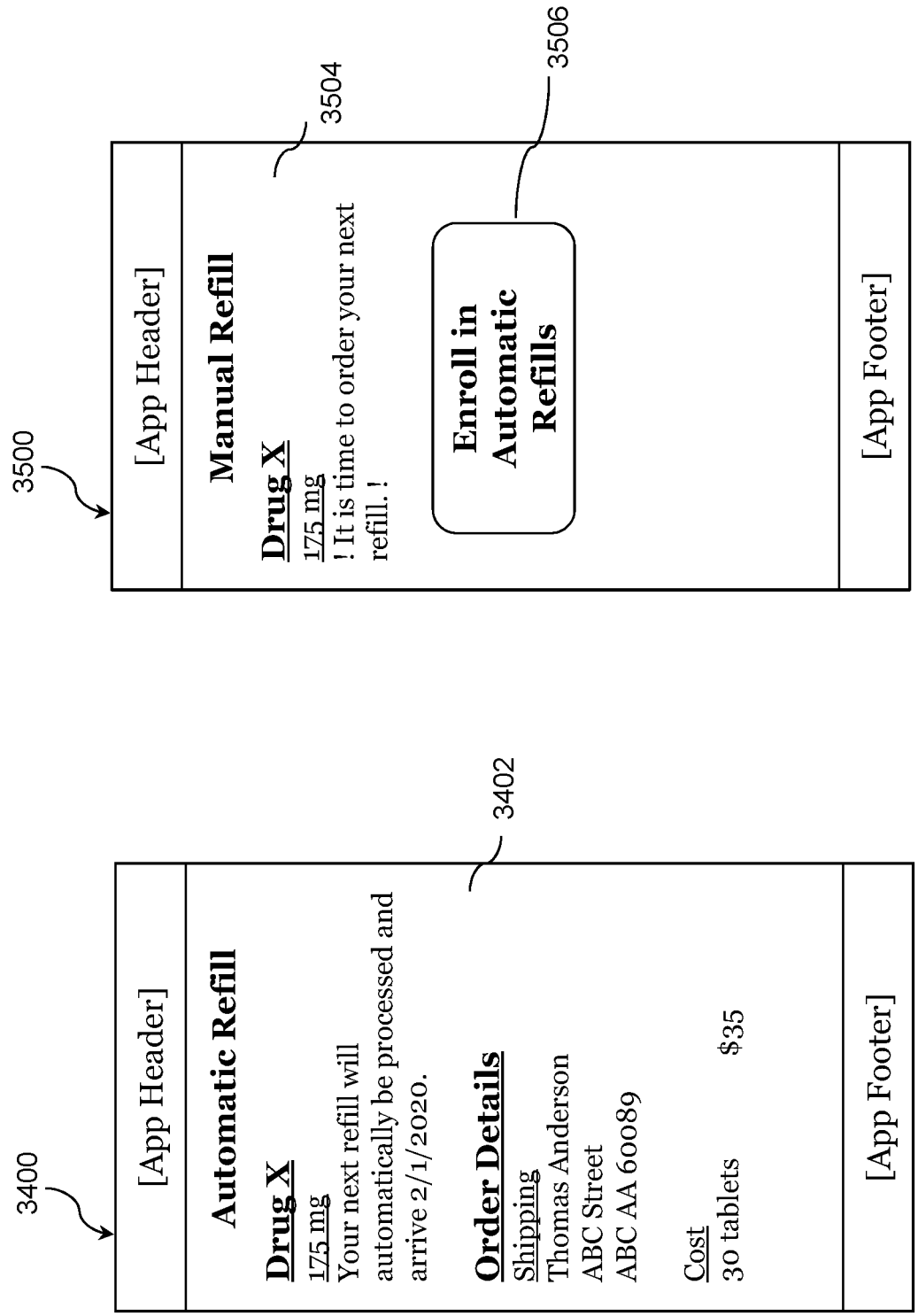

FIG. 34 illustrates third refill message screen 3400. Third refill message screen 3400 is displayed by the patient application when the patient is enrolled to receive automatic refills of their prescription. Third refill message screen 3400 includes a message 3402. Message 3402 indicates whether the prescription of the patient is eligible for automatic refill, when the prescription will be refilled, and order details about the prescription including, for example, the address the prescription with ship to and a cost of the prescription. Third refill message screen 3400 is a dynamic screen that changes when a refill order has been placed, when there are no more refills, etc.

FIG. 35 illustrates fourth refill message screen 3500. Fourth refill message screen 3500 is displayed by the patient application when the patient is not enrolled in automatic refills of their prescription and therefore has to manually refill their prescription. Fourth refill message screen 3500 includes a message 3502. Message 3502 includes a notification indicating whether or not it is time for the prescription to be refilled. Fourth refill message screen 3500 also includes an enrollment button that, when selected, causes the patient application to display an automatic refill enrollment screen (not specifically shown).

Figure 36:
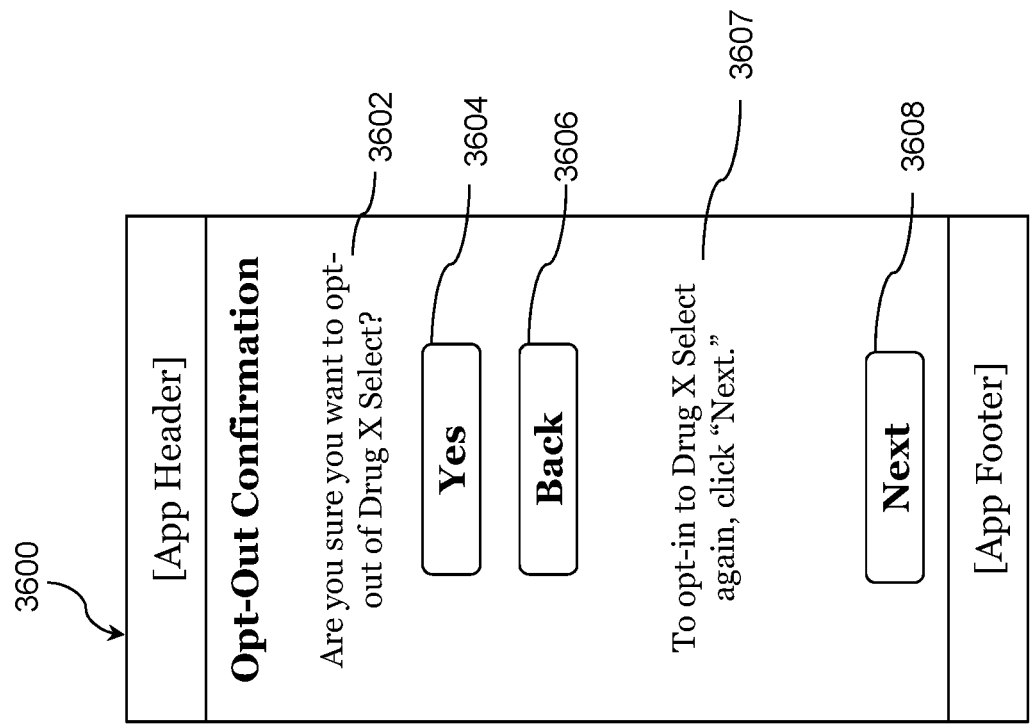

FIG. 36 illustrates an opt-out confirmation screen 3600 that may be displayed by the patient application when the patient wishes to opt-out of the Drug X Select program. Opt-out confirmation screen 3600 includes a first message 3602 asking the patient if they are sure that they want to opt-out of the Drug X Select program. Opt-out confirmation screen 3600 also includes a yes button 3604 and a back button 3606. If the patient selects yes button 3604, the patient application may be caused to display a screen (not specifically shown) indicating that the patient has successfully opted-out of the Drug X Select Program. If the patient selects back button 3606, the patient application may be caused to display, for example, registration screen 1200. Opt-out confirmation screen 3600 also includes a second message 3607 indicating that if the patient wishes to opt-in to the Drug X Select program again, that they should press a next button 3608. When selected, next button 3608 may cause the patient application to display, for example, registration screen 1200.

In other embodiments, the patient application may include additional features and functionality. For example, the patient application may present a user interface to the patient including an option for patient to view or input additional data (e.g., health information including allergies, a prescription list, medical history, etc. and notification preferences) to their profile. The patient application may additionally provide an option for the patient to view their insurance information and how their insurance impacts their prescription. For example, the patient may be able to view a benefits verification and/or prior authorization timeline or status. In one embodiment, a benefits verification may be performed substantially instantaneously from within the patient application. Such information may be accessed (e.g., retrieved or imported) from another source, including a data aggregator (e.g., data aggregator 118), for example. The patient application may also include tutorials (e.g., videos or picture descriptions) of how to administer the prescriptions and other compliance information.

The patient application may additionally enable prescription tracking and management through a user interface of the patient application. For example, the patient may use the patient application to order a prescription refill, set refill or delivery reminders, and/or view prescriber and/or pharmacy information. In some embodiments, the patient application activates a barcode scanner coupled to the computing device executing the patient application and scans a barcode on a received shipment of the medication. The patient application then transmits confirmation of receipt of the medication to a server computer, based on the scanned barcode. The patient application may further facilitate the ordering, tracking, and management of medication-related materials. For example, in some implementations, the patient application displays medication shipping data including a date that the medication was shipped, an expected delivery date, and a tracking number. This allows the patient to use the patient application to track shipments of the prescription product. Shipment tracking information displayed to the patient may be generated, for example, based on data in pharmacy data sources, such as those described herein.

As will be appreciated based on the foregoing specification, the above-described embodiments of the disclosure may be implemented using computer programming or engineering techniques including computer software, firmware, hardware or any combination or subset thereof, wherein the technical effect of the systems and processes described herein is achieved by creating a network-based system for generating and analyzing longitudinal data profiles. Any such resulting program, having computer-readable code means, may be embodied or provided within one or more computer-readable media, thereby making a computer program product, e.g., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

This written description uses examples to disclose the embodiments, including the best mode, and also to enable any person skilled in the art to practice the disclosure, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for fulfilling a prescription of a prescription product for a patient covered by an insurance provider, the system including at least one processor in communication with at least one memory device, the system communicatively coupled between a healthcare provider (HCP) computing device, a pharmacy computing device associated with a pharmacy, a patient computing device, and a plurality of insurance provider databases, wherein the at least one processor is programmed to:

receive, from the HCP computing device, a prescription request including patient data relating to the patient;

determine, in response to receiving the prescription request from the HCP computing device, the insurance provider of the patient based on the received patient data included in the prescription request;

determine, in response to receiving the prescription request from the HCP computing device, by communicating with the plurality of insurance provider databases, an insured cost for the prescription for the patient, wherein the insured cost is a cost the patient will pay for the prescription when a claim is filed with the determined insurance provider;

determine, in response to receiving the prescription request from the HCP computing device, a non-insured cost for the prescription for the patient, wherein the non-insured cost is a cost the patient will pay for the prescription without the claim being filed;

perform a comparison of the insured cost to the non-insured cost to determine which cost is lower;

determine, based on historical data for a plurality of other patients, predicted patient behavior data, wherein the predicted patient behavior data indicates whether the patient is likely to select the insured cost or the non-insured cost;

generate, based on a combination of i) the comparison of the insured cost to the non-insured cost and ii) the predicted patient behavior data, a recommendation for the patient, wherein the recommendation recommends the patient select the insured cost or the non-insured cost;

cause the recommendation to be displayed to the patient;

if the patient selects, based on the recommendation, the insured cost:

transmit, to the patient computing device, a message to the patient including (i) a first payment transaction request prompting the patient to enter payment details for the insured cost, and (ii) an authorization prompt for the patient to authorize the filing of the insurance claim and a first payment transaction for the insured cost; and process the insurance claim and the first payment transaction for the insured cost upon authorization by the patient;

if the patient selects, based on the recommendation, the non-insured cost:

transmit, to the patient computing device, a second payment transaction request prompting the patient to enter payment details for the non-insured cost and authorize a second payment transaction for the non-insured cost; and process the second payment transaction for the non-insured cost upon authorization by the patient; and transmit the prescription to the pharmacy computing device for further processing.

2. The system of claim 1, wherein to determine the insured cost, the processor is configured to:

aggregate, using a data aggregator, insurance data from the plurality of insurance provider databases; and compare the patient data against the aggregated insurance data to determine the insured cost; and wherein to determine the non-insured cost, the processor is configured to retrieve, from a database, the non-insured cost, the non-insured cost taking into account at least one of a coupon, a rebate, and a discount.

3. The system of claim 2, wherein the processor is further configured to:

transmit a message to the patient computing device including a verification request that prompts the patient to verify the determined insurance provider; and transmit a message to the patient computing device notifying the patient of at least one of (i) the pharmacy has received the prescription, (ii) the pharmacy has filled the prescription, and (iii) the pharmacy has mailed the prescription to the patient.

4. The system of claim 1, wherein to determine the insured cost, the processor is further configured to:

receive the insured cost from the pharmacy computing device, wherein the pharmacy computing device determines the insured cost by processing a test claim for the prescription using a pharmacy management system and without actually fulfilling the prescription.

5. The system of claim 1, wherein the system facilitates refilling of the prescription, and wherein the processor is further configured to:

receive a request message for a prescription refill;

determine whether at least one of the insured cost and the non-insured cost has changed since the initial prescription; and transmit a message to the patient computing device if at least one of the insured cost and the non-insured cost has changed, wherein the message includes an updated refill cost and an authorization prompt that prompts the patient to authorize the refill of the prescription.

6. The system of claim 1, wherein the processor is further configured to:

transmit a message to the patient computing device, wherein the message includes at least one of a link to download an application on the patient computing device and an invitation code; and after the application is downloaded, transmit the messages to the application on the patient computing device of the patient.

7. The system of claim 1, wherein the prescription is a prescription for the drug levothyroxine.

8. The system of claim 1, wherein to determine the predicted patient behavior data, the processor is configured to determine the predicted based behavior data by comparing i) the historical data with ii) demographic data for that patient that is included in the patient data.

9. A computer-implemented method for fulfilling a prescription for a patient covered by an insurance provider, the method comprising:

receiving, at a prescription fulfillment system, from a healthcare provider (HCP) computing device, a prescription request including patient data relating to the patient, wherein the prescription fulfillment system is communicatively coupled between the HCP computing device, a pharmacy computing device associated with a pharmacy, a patient computing device, and a plurality of insurance provider databases;

determining, in response to receiving the prescription request from the HCP computing device, the insurance provider of the patient based on the received patient data included in the prescription request;

determining, in response to receiving the prescription request from the HCP computing device, by communicating with the plurality of insurance provider databases, an insured cost for the prescription for the patient, wherein the insured cost is a cost the patient will pay for the prescription when a claim is filed with the determined insurance provider;

determining, in response to receiving the prescription request from the HCP computing device, a non-insured cost for the prescription for the patient, wherein the non-insured cost is a cost the patient will pay for the prescription without the claim being filed;

perform a comparison of the insured cost to the non-insured cost to determine which cost is lower;

determining, based on historical data for a plurality of other patients, predicted patient behavior data, wherein the predicted patient behavior data indicates whether the patient is likely to select the insured cost or the non-insured cost;

generating, based on a combination of i) the comparison of the insured cost to the non-insured cost and ii) the predicted patient behavior data, a recommendation for the patient, wherein the recommendation recommends the patient select the insured cost or the non-insured cost;

transmitting, to the patient computing device, a message to the patient including the recommendation;

receiving a user selection of the insured cost or the non-insured cost for the prescription;

when the user selection is for the insured cost:

transmitting, to the patient computing device, a message to the patient including (i) a first payment transaction request prompting the patient to enter payment details for the insured cost, and (ii) an authorization prompt for the patient to authorize the filing of the insurance claim and a first payment transaction for the insured cost; and processing the insurance claim and the first payment transaction for the insured cost upon authorization by the patient;

when the user selection is for the non-insured cost:

transmitting, to the patient computing device, a second payment transaction request prompting the patient to enter payment details for the non-insured cost and authorize a second payment transaction for the non-insured cost; and processing the second payment transaction for the non-insured cost upon authorization by the patient; and transmitting the prescription to the pharmacy computing device for further processing.

10. The computer-implemented method of claim 9, wherein determining the insured cost comprises:

aggregating, using a data aggregator, insurance data from the plurality of insurance provider databases; and comparing the patient data against the aggregated insurance data to determine the insured cost; and wherein determining the non-insured cost comprises retrieving, from a database, the non-insured cost, the non-insured cost taking into account at least one of a coupon, a rebate, and a discount.

11. The computer-implemented method of claim 10, wherein the method further comprises:

transmitting a message to the patient computing device including a verification request for the patient to verify the determined insurance provider; and transmitting a message to the patient computing device notifying the patient of at least one of (i) the pharmacy has received the prescription, (ii) the pharmacy has filled the prescription, and (iii) the pharmacy has mailed the prescription to the patient.

12. The computer-implemented method of claim 9, wherein the method further comprises:

receiving the insured cost from the pharmacy computing device, wherein the pharmacy computing device determines the insured cost by processing a test claim for the prescription using a pharmacy management system and without actually fulfilling the prescription.

13. The computer-implemented method of claim 9, wherein the method further comprises:

receiving a request message for a prescription refill from the HCP computing device;

determining that the non-insured cost has changed since the initial prescription; and transmitting a message to the patient computing device indicating that the non-insured cost has changed, wherein the message includes an updated refill cost and an authorization prompt that prompts the patient to authorize the refill of the prescription.

14. The computer-implemented method of claim 9, wherein the method further comprises:

transmitting a message to the patient computing device, wherein the message includes at least one of a link to download an application and an invitation code; and after the application is downloaded, transmitting the messages to the application on the patient computing device of the patient.

15. At least one non-transitory computer-readable media having computer-executable instructions thereon, wherein when executed by at least one processor of a prescription fulfillment system, cause the at least one processor to:

receive, from a healthcare provider (HCP) computing device, a prescription request including patient data relating to a patient, the processor communicatively coupled between the HCP computing device, a pharmacy computing device associated with a pharmacy, a patient computing device, and a plurality of insurance provider databases;

determine, in response to receiving the prescription request from the HCP computing device, an insurance provider of the patient based on the received patient data included in the prescription request;

determine, in response to receiving the prescription request from the HCP computing device, by communicating with the plurality of insurance provider databases, an insured cost for a prescription for the patient, wherein the insured cost is a cost the patient will pay for the prescription when a claim is filed with the determined insurance provider;

determine, in response to receiving the prescription request from the HCP computing device, a non-insured cost for the prescription for the patient, wherein the non-insured cost is a cost the patient will pay for the prescription without the claim being filed;

perform a comparison of the insured cost to the non-insured cost to determine which cost is lower;

determine, based on historical data for a plurality of other patients, predicted patient behavior data, wherein the predicted patient behavior data indicates whether the patient is likely to select the insured cost or the non-insured cost;

generate, based on a combination of i) the comparison of the insured cost to the non-insured cost and ii) the predicted patient behavior data, a recommendation for the patient, wherein the recommendation recommends the patient select the insured cost or the non-insured cost;

cause the recommendation to be displayed to the patient;

if the patient selects, based on the recommendation, the insured cost:

transmit, to the patient computing device, a message to the patient including (i) a first payment transaction request prompting the patient to enter payment details for the insured cost, and (ii) an authorization prompt for the patient to authorize the filing of the insurance claim and a first payment transaction for the insured cost; and process the insurance claim and the first payment transaction for the insured cost upon authorization by the patient;

if the patient selects, based on the recommendation, the non-insured cost:

transmit, to the patient computing device, a second payment transaction request prompting the patient to enter payment details for the non-insured cost and authorize a second payment transaction for the non-insured cost; and process the second payment transaction for the non-insured cost upon authorization by the patient; and transmit the prescription to the pharmacy computing device for further processing.

16. The computer-readable media of claim 15 further causing the at least one processor to, in transmitting the prescription, transmit the prescription to the pharmacy computing device to cause the pharmacy to fill the prescription and mail the filled prescription to the patient.

17. The computer-readable media of claim 16 further causing the at least one processor to:

transmit a message to the patient computing device including a verification request for the patient to verify the determined insurance provider; and transmit a message to the patient computing device notifying the patient of at least one of (i) the pharmacy has received the prescription, (ii) the pharmacy has filled the prescription, and (iii) the pharmacy has mailed the prescription to the patient.

18. The computer-readable media of claim 15 further causing the at least one processor to:
receive the insured cost from the pharmacy computing device, wherein the pharmacy computing device determines the insured cost by processing a test claim for the prescription using a pharmacy management system and without actually fulfilling the prescription.

19. The computer-readable media of claim 15 further causing the at least one processor to:
receive a request message for a prescription refill from the HCP computing device;
determine whether at least one of the insured cost and the non-insured cost has changed since the initial prescription; and
transmit a message to the patient computing device if at least one of the insured cost and the non-insured cost has changed, wherein the message includes an updated refill cost and an authorization prompt that prompts the patient to authorize the refill of the prescription.

20. The computer-readable media of claim 15 further causing the at least one processor to:
transmit a message to the patient computing device of the patient, wherein the message includes at least one of a link to download an application on the patient computing device and an invitation code; and
after the application is downloaded, transmit the messages to the application on the patient computing device of the patient.

* * * * *